United States Patent [19]

Miyasaka et al.

[11] Patent Number: 4,604,463

[45] Date of Patent: Aug. 5, 1986

[54] CAMPTOTHECIN DERIVATIVES AND PROCESS FOR PREPARING SAME

[75] Inventors: Tadashi Miyasaka, Kanagawa; Seigo Sawada, Tokyo; Kenichiro Nokata, Tokyo; Eiichi Sugino, Tokyo; Masahiko Mutai, Tokyo, all of Japan

[73] Assignee: Kabushiki Kaisha Yakult Honsha, Tokyo, Japan

[21] Appl. No.: 627,980

[22] Filed: Jul. 5, 1984

[30] Foreign Application Priority Data

Jul. 14, 1983 [JP] Japan ............................ 58-126946

[51] Int. Cl.⁴ .......................................... C07D 491/22
[52] U.S. Cl. ................................. 544/125; 544/60;
544/361; 546/48
[58] Field of Search ............... 546/48; 544/361, 125, 544/60

[56] References Cited

U.S. PATENT DOCUMENTS

| | | |
|---|---|---|
| 3,894,029 | 7/1975 | Winterfeldt et al. ............... 546/48 |
| 4,031,098 | 6/1977 | Sugasawa .............................. 546/48 |
| 4,399,276 | 8/1983 | Miyasaka et al. ..................... 546/48 |
| 4,399,282 | 8/1983 | Miyasaka et al. ..................... 546/48 |
| 4,473,692 | 9/1984 | Miyasaka et al. ..................... 546/48 |

FOREIGN PATENT DOCUMENTS

| | | |
|---|---|---|
| 74770 | 3/1983 | European Pat. Off. ............ 546/48 |
| 74256 | 3/1983 | European Pat. Off. ............ 546/48 |
| 88642 | 8/1983 | European Pat. Off. ............ 546/48 |
| 154583 | 9/1983 | Japan ................................... 546/48 |
| 154584 | 9/1983 | Japan ................................... 546/48 |
| 51289 | 3/1984 | Japan ................................... 546/48 |

*Primary Examiner*—George F. Lesmes
*Assistant Examiner*—S. A. Gibson
*Attorney, Agent, or Firm*—Birch, Stewart, Kolasch & Birch

[57] ABSTRACT

New camptothecin derivatives possessing high antitumor activity with slight toxicity, represented by the general formula:

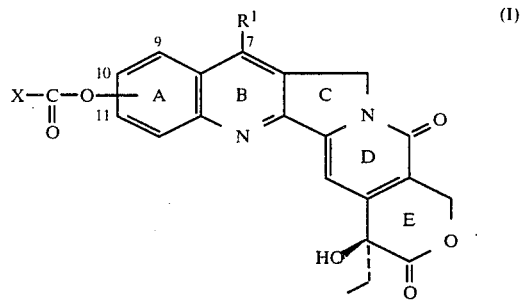

wherein $R^1$ is a hydrogen atom, a halogen atom or an alkyl group with 1-4 carbon atoms and X is a chlorine atom or $-NR^2R^3$ where $R^2$ and $R^3$ are the same or different and each represents a hydrogen atom, a substituted or unsubstituted alkyl group with 1-4 carbon atoms or a substituted or unsubstituted carbocyclic or heterocyclic group, with the proviso that when both $R^2$ and $R^3$ are the substituted or unsubstituted alkyl groups, they may be combined together with the nitrogen atom, to which they are bonded, to form a heterocyclic ring which may be interrupted with $-O-$, $-S-$ and/or $>N-R^4$ in which $R^4$ is a hydrogen atom, a substituted or unsubstituted alkyl group with 1-4 carbon atoms or a substituted or unsubstituted phenyl group and wherein the grouping $-O-CO-X$ is bonded to a carbon atom located in any of the 9-, 10- and 11-positions in the ring A of camptothecin, as well as an ammonium salt or an alkali metal salt thereof. These new camptothecin derivatives are prepared by reacting a 7-$R^1$-camptothecin derivative having a hydroxyl group in any of the 9-, 10- and 11-positions on the ring A thereof with phosgen and then reacting, if necessary, the resultant 7-$R^1$-camptothecin derivative having a chlorocarbonyloxy group in the same position on the ring A thereof with an amine $HNR^2R^3$ or by reacting a 7-$R^1$-camptothecin derivative having a hydroxyl group in any of the 9-, 10- and 11-positions on the ring A thereof with a carbamoyl chloride Cl-CONR²R³.

25 Claims, No Drawings

CAMPTOTHECIN DERIVATIVES AND PROCESS FOR PREPARING SAME

BACKGROUND OF THE INVENTION

1. Field of the Invention

The present invention relates to new camptothecin derivatives possessing anti-tumor activity and to a process for preparing such derivatives. More particularly, the present invention relates to new camptothecin derivatives carrying an aminocarbonyloxy group or a chlorocarbonyloxy group in any of the 9-, 10- and 11-positions on the ring A thereof and possessing excellent anti-tumor activity with a low level of toxicity as well as a process for the preparation of the new camptothecin derivatives.

2. Description of the Prior Art

Camptothecin is an alkaloid extracted and isolated from *Camptotheca accuminata* (Nyssaceae), etc., which has a pentacyclic structure consisting of a characteristic fused 5-ring system consisting of quinoline (rings A and B), pyrroline (ring C), α-pyridone (ring D) and a six-membered lactone (ring E) and is distinguished by displaying a strong inhibitory activity toward biosynthesis of nucleic acid. In addition, camptothecin is a unique anti-tumor substance characterized by its rapid and reversible action, its lack of any cross-tolerance with the existing anti-tumor agents and by exhibiting a strong anti-tumor activity against experimentally transplanted carcinoma such as leukemia L-1210 in mice or Walker 256 tumor in rats. Although camptothecin is still regarded as one of the most potent substances possessing anti-tumor activity, the use of this compound itself for clinical treatments is significantly limited because of high toxicity. Moreover, camptothecin and the majority of derivatives thereof are sparingly soluble in water and thus involve a problem in case of administration as medicaments.

Accordingly, a number of attempts have been made not only to reduce toxicity of camptothecin while maintaining its anti-tumor activity by converting camptothecin chemically into its derivatives but also to make camptothecin and derivatives thereof easily soluble in water by chemical modifications of the camptothecin molecule or substituents therein. The chemical modifications so far reported are mainly about the ring D and/or E of camptothecin. As a method for making camptothecin or derivatives thereof soluble in water, for example, a ring-opening reaction for the E-ring (lactone ring) of camptothecin was used in the prior arts to form an alkali metal salt of the carboxyl function. However, any chemical modification of the ring D and/or E, including such ring-opening reaction, revealed only failure in maintaining anti-tumor activity and very poor improvement in toxicity [J. Med. Chem., 19 (1976), 675]. From the chemotherapeutic point of view, therefore, it is of importance that the chemical modifications of camptothecin should be restricted in the rings A, B and C without effecting any change in the rings D and E which are believed to be the essential structural elements for the expression of the above mentioned characteristic biological activities.

Except for a method for functionalizing the 12-position of camptothecin reported in 1976 which comprises a series of many troublesome conversion and purification operations starting with a relatively easily operable nitration at the 12-position [P. Pei-chuang et al., Hau Hsueh Hsueh Pao 33 (1975), 71; Chem. Abstr. 84 (1976) 115629p], no success was reported until 1979 in connection with chemical functionalization of camptothecin in a moiety involving the rings A, B and C. This is probably ascribable to the reasons that camptothecin itself is only sparingly soluble in various organic solvents and that camptothecin possessing the molecular nature of heterocyclic rings is resistant to the so-called electronphilic reactions conventionally carried out on aromatic rings. In the present status, such obstacles strongly discourage chemical modifications of camptothecin contemplated academically for preparing new classes of derivatives thereof.

Under the above mentioned circumstances, the present inventors previously found together with co-workers processes for preparing 5- and 7-substituted camptothecins (U.S. Pat. No. 4,399,282) by introducing (1) a hydroxymethyl group into the 7-position of camptothecin by subjecting camptothecin to a radical reaction with methanol by the aid of sulfuric acid and a peroxide, (2) a hydroxy group into the 5-position of camptothecin by treating camptothecin with sulfuric acid, water and a persulfate in the presence of a metal ion or by treating camptothecin with iodine in the presence of a base, and (3) an alkyl or aralkyl group into the 7-position of camptothecin by subjecting camptothecin to a radical reaction with a compound of the general formula: RX (wherein R stands for an alkyl group or an aralkyl group, and

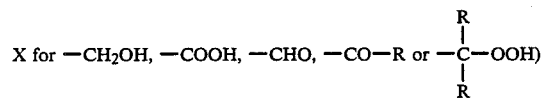

X for —CH$_2$OH, —COOH, —CHO, —CO—R or —C(R)(R)—OOH)

preferably in a large excess amount by the aid of sulfuric acid, water and a peroxide in the presence of a metal ion. Further, the present inventors prepared together with co-workers a great number of new camptothecin derivatives from these 5- and 7-substituted camptothecin derivatives (U.S. Pat. Nos. 4,399,276 and 4,399,282) according to the process wherein 7-hydroxymethylcamptothecin is acylated with an acylating agent to obtain 7-acyloxymethylcamptothecins or 20-O-acyl-7-acyloxymethylcamptothecins or wherein 7-hydroxymethylcamptothecin is oxidized with an oxidizing agent usually capable of oxidizing a hydroxymethyl group to a carboxyl group to obtain 7-carboxycamptothecin, which is then esterified with an alcohol to obtain 7-alkoxycarbonylcamptothecins, the process wherein 5-alkoxycamptothecins are obtained by dissolving 5-hydroxycamptothecin in a lower alcohol, adding thereto an acid and heating the mixture, or wherein 5-acyloxycamptothecins or 20-O-acyl-5-acyloxycamptothecins are obtained by acylating 5-hydroxycamptothecin with a reactive acid derivative such as an acid anhydride or a halide of a carboxylic acid, the process wherein camptothecin-7-aldehyde is obtained by treating the 7-hydroxymethylcamptothecin with various cationoid reagents without using any oxidizing agent, and the process wherein 7-alkoxymethylcamptothecins and 7-dialkoxymethylcamptothecins are obtained by treating 7-hydroxymethylcamptothecin in a lower alkanol or an aralkyl alcohol with an acid.

Further successively, the present inventors prepared together with co-workers camptothecin-1-oxide or 7- or 5-substituted derivatives thereof by treating camptothecin or a 7- or 5-substituted derivative thereof with an N-oxidizing agent (Japanese Laid-open Patent Appln. No. 58-39685; U.S. Ser. No. 414,528) as well as various 10-substituted camptothecin derivatives according to the process wherein camptothecin-1-oxide or a 7- or 5-substituted derivative thereof obtained as above is reacted with an active hydrogen-containing reagent in the presence of an acid under irradiation of UV-rays (Japanese Laid-open Patent Appln. No. 58-39683; U.S. Ser. No. 413,879) or the process wherein camptothecin is first catalytically hydrogenated and the resultant 1,2,6,7-tetrahydrocamptothecin is treated with an acylating agent and then with a mixture of nitric acid and sulfuric acid to form a 1-acyl-10-nitro-1,2,6,7-tetrahydrocamptothecin which is then deacylated and oxidized to 10-nitrocamptothecin and is then modified in various manners known per se to convert the 10-nitro group into other 10-substituents, e.g. 10-hydroxy group (Japanese Laid-open Patent Applns. Nos. 58-134095 and 58-152888; U.S. Ser. No. 413,879).

It was also found that when camptothecin in sulfuric acid was treated carefully with nitric acid under ice-cooling and agitation, new 9-nitrocamptothecin could be obtained in a yield of 30–40% together with the known 12-nitrocamptothecin. This new 9-nitrocamptothecin is then reduced to 9-aminocamptothecin which can be converted into various 9-substituted camptothecin derivatives according to the methods known per se as in the case of 10-nitrocamptothecin (Japanese Laid-open Patent Appln. No. 59-51289). For example, 9-aminocamptothecin can be converted into the corresponding 9-halogeno or 9-cyano derivative by once converting the 9-amino derivative into 9-diazonium salt and then treating the salt with cuprous halide or cyanide according to the Sandmayer reaction. Further, 9-diazonium salt can be converted into 9-hydroxy, 9-alkoxy and 9-acyloxy derivatives in the manner known per se.

Various 11-substituted camptothecin derivatives were prepared by catalytically hydrogenating camptothecin to form 1,2,6,7-tetrahydrocamptothecin, treating this tetrahydro derivative directly with sulfuric acid and nitric acid whereby the 11-position of camptothecin was selectively nitrified to form 11-nitro-1,2,6,7-tetrahydrocamptothecin, oxidizing the 11-nitro- 1,2,6,7-tetrahydrocamptothecin to 11-nitrocamptothecin, and thereafter converting the 11-nitro group in the resultant compound into various 11-substituents, as in the case of 10-nitrocamptothecin, according to the methods known per se (Japanese Laid-open Patent Appln. No. 59-51987). For example, the 11-nitro group thus formed can first be converted into an 11-amino group by reduction according to Clemensen or the like method and the latter 11-amino group can further be converted into an 11-hydroxy group by diazotization with a nitrite under cooling and acidic conditions followed by hydrolysis under warming and weakly alkaline conditions.

From the studies on various camptothecin derivatives prepared heretofore, the present inventors obtained an interesting result that introduction of an alkyl group into the 7-position of camptothecin tends to enhance anti-tumor activity while introduction of a hydroxyl group into the ring A of camptothecin tends to reduce toxicity without sacrificing the anti-tumor activity. For further extensive researches based on this interesting result for clarifying the relation between the substituents and locations thereof in camptothecin structure and pharmacological properties including toxicity, therefore, there is still a great demand in this art for developing further new classes of camptothecin derivatives carrying various substituents especially in 7-position and on the ring A of camptothecin skeleton.

BRIEF SUMMARY OF THE INVENTION

Accordingly, it is an object of the present invention to provide new camptothecin derivatives substituted or unsubstituted in the 7-position thereof and carrying an acyloxy group (more precisely, an aminoacyloxy group) or a chloroacyloxy group in any of the 9-, 10- and 11-positions on the ring A thereof.

It is another object of the present invention to provide new camptothecin derivatives which are strong in anti-tumor activity and possess good solubility in water and an extremely low toxicity.

It is still another object of the present invention to provide a process for the preparation of various camptothecin derivatives carrying an acyloxy group in any of the 9-, 10- and 11-positions thereof according to an easy and economically advantageous operations.

It is a further object of the present invention to provide a new means for introducing an aminocarbonyloxy group or a chlorocarbonyloxy group into any of the 9-, 10- and 11-positions of camptothecin or a 7-substituted derivative thereof.

It is a still further object of the present invention to provide a new means for solubilizing camptothecin or a derivative thereof in water without causing any serious reduction in anti-tumor activity.

Other objects, features and advantages of the present invention will become apparent more fully from the following description.

DETAILED DESCRIPTION OF THE INVENTION

With an attempt to prepare a new class of camptothecin derivatives which are strong in inherent anti-tumor activity and possess good solubility in water with an extremely low toxicity, the present inventors have made extensive researches for making chemical modifications in the 9-, 10- and 11-positions of camptothecin structure, using camptothecin derivatives already reported or prepared by the present inventors and coworkers which carry a hydroxyl group in any of the 9-, 10- and 11-positions as starting materials, taking careful attention to the chemical modification so that a solubilizing function may be contained in a substituent to be introduced and lest any destroy should occur in the other ring structures, especially in the ring D and/or E. As a result of the extensive researches, it has now been found surprisingly that new camptothecin derivatives of the expected pharmacological properties can be obtained by combining with the hydroxyl group existing in any of the 9-, 10- and 11-positions a chemically stable aminocarbonyl or chlorocarbonyl group which contains a solubilizing function and can be split off enzymatically in vivo. It has also been found incidentally that introduction of such an aminocarbonyl or chlorocarbonyl group into the hydroxyl group in any of the 9-, 10- and 11-positions on the ring A of camptothecin can be achieved by treating a camptothecin derivative carrying a hydroxyl group in any of the 9-, 10- and 11-positions thereof with phosgene and optionally reacting the resultant chlorocarbonyloxy derivative with an amine, or alternatively by treating the camptothecin derivative carrying a hydroxyl group in any of the 9-, 10- and 11-positions thereof directly with a reactive functional derivative of a carbamic acid.

A new class of camptothecin derivatives carrying such aminocarbonyloxy or chlorocarbonyloxy group thus obtained are improved in pharmacological properties and extremely reduced in toxicity. The present invention has been accomplished on the basis of the above finding.

In accordance with the present invention, there are provided new camptothecin derivatives of the general formula:

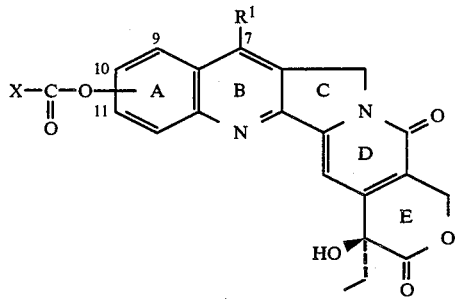

wherein $R^1$ is a hydrogen atom, a halogen atom or an alkyl group with 1–4 carbon atoms and X is a chlorine atom or $-NR^2R^3$ where $R^2$ and $R^3$ are the same or different and each represents a hydrogen atom, a substituted or unsubstituted alkyl group with 1–4 carbon atoms or a substituted or unsubstituted carbocyclic or heterocyclic group, with the proviso that when both $R^2$ and $R^3$ are the substituted or unsubstituted alkyl groups, they may be combined together with the nitrogen atom, to which $R^2$ and $R^3$ are bonded, to form a heterocyclic ring which may be interrupted with $-O-$, $-S-$ and/or $>N-R^4$ in which $R^4$ is a hydrogen atom, a substituted or unsubstituted alkyl group with 1–4 carbon atoms or a substituted or unsubstituted phenyl group, and wherein the grouping $-O-CO-X$ is bonded to a carbon atom located in any of the 9-, 10- and 11-positions in the ring A of camptothecin, as well as an ammonium salt or an alkali metal salt thereof.

In the general formula (I), the radical $R^1$ located in 7-position of the ring B is preferably a halogen atom or an alkyl group with 1–4 carbon atoms, with the alkyl group being most preferable. The acyloxy grouping $-O-CO-X$ can be bonded to a carbon atom located in any of the 9-, 10- and 11-positions in the ring A of camptothecin but is preferably bonded to the 10-position thereof.

Examples of $R^1$ being a halogen atom include fluorine atom, chlorine atom, bromine atom and iodine atom, with the fluorine and chlorine atoms being preferable. Illustrative of $R^1$, $R^2$, $R^3$ or $R^4$ in case of an alkyl group with 1–4 carbon atoms are straight or branched chain $C_{1-4}$ alkyl groups, i.e. methyl, ethyl, propyl, isopropyl, n-butyl, isobutyl and tert.-butyl groups, with the methyl and ethyl groups being preferable.

When $R^2$, $R^3$ or $R^4$ is an alkyl group with 1–4 carbon atoms as exemplified above, it may be substituted by one or more substituents selected from the following atoms and/or groups:

| | |
|---|---|
| $-F$, $-Cl$, $-Br$ and $-I$ (halogen atoms), | (A) |
| $-OH$ and $-OR^5$ (hydroxy, alkoxy and phenoxy groups), | (B) |
| $-COOR^6$, $-SO_3R^6$ and $-PO_3(R^6)_2$ (acid functions), | (C) |

-continued

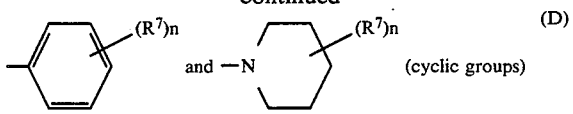

| | |
|---|---|
| $-NR^8R^9$ and $-CONR^8R^9$ (amino and amido groups), and | (E) |
| $-Q-A-OR^5$, $-Q-A-NR^8R^9$ and | (F) |
| $-Q-A-Q-R^5$ (ester groups) | | wherein $R^5$ is an alkyl group with 1–4 carbon atoms or a phenyl group which may be substituted by a halogen atom or an alkyl group with 1–4 carbon atoms, $R^6$ is a hydrogen atom or an alkyl group with 1–4 carbon atoms, $R^7$ is a hydrogen atom, a halogen atom, an alkyl group with 1–4 carbon atoms or an alkoxy group with 1–4 carbon atoms, n is an integer of 1–3, $R^8$ and $R^9$ are the same or different and each represents a hydrogen atom or an alkyl group with 1–4 carbon atoms with the proviso that when both $R^8$ and $R^9$ are the alkyl groups, they may be combined together with the nitrogen atom, to which they are bonded, to form a heterocyclic ring which may be interrupted with $-O-$, $-S-$ or $>N-R^6$, Q is the grouping $-O-CO-$ or $-CO-O-$, and A is a straight or branched chain alkylene group with 1–4 carbon atoms.

In the case (A), preferable halogen atoms are fluorine and chlorine atoms. Examples of the halogen-substituted alkyl group include fluoromethyl, 2-fluoroethyl, trifluoromethyl, chloromethyl, 1- or 2-chloroethyl, 3-chloro-n-propyl, dichloromethyl, 1,2-dichloroethyl, trichloromethyl, bromomethyl, 1- or 2-bromoethyl, dibromomethyl, 1,2-dibromoethyl, tribromomethyl and iodomethyl groups. When two or more halogen atoms are present in the alkyl group, they may be the same or different such as fluorochloromethyl or 1-chloro-2-bromoethyl.

In the case (B), the alkyl group desirably contains one hydroxyl group. Preferable examples of the hydroxyl-substituted alkyl group include hydroxymethyl, 1-hydroxyethyl, 2-hydroxyethyl and 3-hydroxypropyl group. When $R^5$ is an alkyl group with 1–4 carbon atoms, the substituent is an alkoxy group with 1–4 carbon atoms and this case just corresponds to the case (D) wherein $R^7$ is an alkoxy group with 1–4 carbon atoms. In these cases, the alkyl moiety of the alkoxy group corresponds in principle to the aforesaid alkyl group with 1–4 carbon atoms. Illustrative of such alkoxy group are methoxy, ethoxy, propoxy, isopropoxy, n-butoxy, isobutoxy and tert-butoxy groups. Preferable examples of the alkyl group substituted by such alkoxy group or groups include methoxymethyl, 2-methoxyethyl, 3-methoxypropyl, 4-methoxybutyl, ethoxymethyl, 2-ethoxyethyl, 3-ethoxypropyl, propoxymethyl, 2-propoxyethyl, 3-propoxypropyl, 4-propoxybutyl, dimethoxymethyl, 2,2-dimethoxyethyl, diethoxymethyl, 2,2-diethoxyethyl, dipropoxymethyl and 2,2-dipropoxyethyl groups. In case of $R^5$ being a substituted or unsubstituted phenyl group, preferable examples of the phenyl-substituted alkyl group include phenoxymethyl, p-methylphenoxymethyl, o-chlorophenoxymethyl, 2-phenoxyethyl, 3-phenoxypropyl and 4-phenoxybutyl group.

In the case (C), the substituents having acid function are usually present in the form of an ester with a lower alkanol with 1–4 carbon atoms, in particular with methanol or ethanol, and in some cases as alkali metal salts or ammonium salts. Thus, $R^6$ is preferably an alkyl group with 1–4 carbon atoms as exemplified with respect to $R^1$–$R^4$. Illustrative of the alkyl group substituted by such acids or esters thereof are, for example, carboxymethyl, methoxycarbonylmethyl, ethoxycarbonylmethyl, 2-ethoxycarbonylethyl, ethoxysulfonylmethyl and diethoxyphosphonylmethyl groups. The substituents in the form of esters can easily be saponified, if desired, to the free carboxylic, sulfonic and phosphonic acid groups or the alkali metal salts thereof.

In the case (D), the phenyl group is preferably substituted by one substituent $R^7$ in any desired position but may be substituted by two or three substituents $R^7$ which may be the same or different. When two substituents $R^7$ are present in the phenyl group, they are preferably present in 2- and 4-positions or 2- and 6-positions. When three substituents $R^7$ are present in the phenyl group, they are preferably located in 2-, 4- and 6-positions. When $R^7$ is a halogen atom, the phenyl group preferably has one fluorine, chlorine or bromine atom but may have up to 3 halogen atoms as mentioned above. When $R^7$ is an alkyl or alkoxy group with 1–4 carbon atoms, the alkyl moiety of such group just corresponds to the alkyl group as exemplified with respect to $R^1$–$R^4$. Illustrative of the phenyl-substituted alkyl group are, for example, benzyl, phenethyl, 3-phenylpropyl, 4-phenylbutyl, 2-fluorobenzyl, 2-chlorobenzyl, 4-ethylbenzyl, 4-n-propylbenzyl, 4-methoxybenzyl, 4-fluorophenethyl, 4-methoxyphenethyl, 2,4-dichlorobenzyl, 2,4-dimethylbenzyl, 2,4-dimethoxybenzyl, 2,4,6-trichlorobenzyl, 2,4-dichlorophenethyl, 3-(2,4-dimethoxyphenyl)propyl, 3-(4-ethylphenyl)propyl, 3-(4-propoxyphenyl)propyl and 3-(2,4-dibutoxyphenyl)propyl groups.

In case of $R^2$ or $R^3$ being an alkyl group carrying a piperidyl group as a substituent thereof, the piperidyl group is present as a rule in the $\omega$-position of the alkyl group. Typical examples of such piperidyl-(1)-alkyl group include 1-piperidylmethyl, 2-(1-piperidyl)ethyl, 3-(1-piperidyl)propyl and 4-(1-piperidyl)butyl groups. The piperidyl group is preferably not substituted ($R^7$=H) but may be substituted with 1-3 alkyl, alkoxy and/or halogen substituents ($R^7 \neq H$) in the same manner as in the case of the phenyl-substituted alkyl groups.

In the case (E), at least one of the groups $R^8$ and $R^9$ as well as $R^6$ is preferably an alkyl group with 1–4 carbon atoms as exemplified with respect to $R^1$–$R^4$. Preferable examples of the grouping $NR^8R^9$ and of the amino moiety $NR^8R^9$ in the grouping $CONR^8R^9$ include amino, N-methylamino, N-ethylamino, N-propylamino, N-butylamino, N,N-dimethylamino, N,N-diethylamino, N-methyl-N-ethylamino, N,N-dipropylamino, N,N-dibutylamino and heterocyclic groups such as 1-piperidino, 4-morpholino and 4-methyl-1-piperazino groups.

In the case (F), the substituent groupings can be regarded as ester components. In case of —Q—A—$OR^5$ wherein Q is —CO—O—, an alkylenediol —A—$OR^5$ is linked with the alkyl group through the carboxyl function. In case of —Q—A—$OR^5$ wherein Q is —O—CO—, a hydroxy acid is linked with a hydroxy-substituted alkyl group in the case (B). In case of —Q—A—$NR^8R^9$ wherein Q is —O—CO—, the alkyl group substituted by hydroxyl group in the case (B) is esterified with an amino acid. In case of —Q—A—Q—$R^5$ wherein Q—A—Q is —O—CO—A—CO—O—, the alkyl group sustituted by hydroxyl group in the case (B) is linked with a dicarboxylic acid or a hemiester thereof. The group A is derived in principle from the alkyl groups as exemplified above and is preferably methylene, ethylene or propylene-1,3. Examples of the alkyl group substituted by such ester components include methoxyethoxycarbonylethyl, hydroxymethylcarbonyloxymethyl, glycyloxymethyl, dimethylaminoethylcarbonyloxymethyl and methoxycarbonylethylcarbonyloxymethyl (methoxysuccinyloxymethyl) group.

In case $R^2$ or $R^3$ is a carbocyclic or heterocyclic group which may be substituted, such cyclic ring is preferably saturated but may be of aromatic nature and is usually selected from cycloalkyl, phenyl and saturated or unsaturated aromatic heterocyclic groups. As substituents on such cyclic group, a halogen atom such as fluorine, chlorine or bromine atom, an alkyl group with 1–4 carbon atoms and an alkoxy group with 1–4 carbon atoms are useful. Examples of the saturated carbocyclic and heterocyclic groups include cyclopentyl, cyclohexyl, N-methyl-piperidyl-(4) and 2-pyrrolidyl groups. Examples of the carbocyclic and heterocyclic groups of aromatic nature include phenyl, tolyl, xylyl, pyridyl-2 and 2-methylpyridyl-(4) groups.

When alkyl groups $R^2$ and $R^3$ are combined to form a heterocyclic ring together with the nitrogen atom to which they are bonded, such nitrogen-containing heterocyclic group is selected from 5-membered and 6-membered saturated heterocyclic groups such as pyrrolidino and piperidino groups. This heterocyclic ring system may be interrupted with —O—, —S— or

to form, for example, 2-oxapyrrolidino, morpholino, thiomorpholino, piperazino and 4-$C_{1-4}$ alkylpiperazino groups. Preferable heterocyclic groups are pyrrolidino, piperidino, morpholino, piperazino and 4-$C_{1-4}$ alkylpiperazino groups. If $R^4$ on the 4-nitrogen atom of the piperazino ring is a substituted alkyl group, it may carry a substituent or substituents selected from the atoms and/or groups shown in the cases (A)–(F). Examples of such substituted alkyl group $R^4$ include 2-bromoethyl, ethoxymethyl, methoxycarbonylmethyl, 2-ethylbenzyl, 2-(1-piperidyl)ethyl, N-methylaminomethyl, N,N-diethylaminomethyl, N-isopropylcarbamoylmethyl, 2-ethoxy-ethoxycarbonylmethyl, N,N-dimethylaminomethoxycarbonylmethyl and 4-ethoxycarbonylbutylcarbonyloxymethyl groups.

When either or both of the alkyl groups $R^2$ and $R^3$ are substituted by a substituent or substituents selected from the atoms and/or groups shown in the cases (A)–(F) and are combined to form such heterocyclic ring together with the nitrogen atom to which $R^2$ and $R^3$ are bonded, the substituent or substituents in the alkyl groups $R^2$ and/or $R^3$ will form a ring substituent or substituents in the resultant heterocyclic group and/or a side chain or chains extending from the alkyl main chain on the heterocyclic ring. For example, 3-(1-piperidyl)-propyl as $R^2$ and ethyl as $R^3$ are combined together with the nitrogen atom, to which they are bonded, to form 4-[(1-piperidino)-1-piperidino]. Likewise, 3-(1-piperidyl)propyl as $R^2$ and 1-chloroethyl as $R^3$ are combined together with the nitrogen atom, to which they are bonded, to form 4-[1-piperidyl)-1-(2-chloro)-piperidino]. In case 3-dimethylaminopropyl as $R^2$ and 1-chloroethyl as $R^3$ are combined together with the nitrogen atom to which they are bonded, a 2-chloro-4-dimethylamino-1-piperidino group is formed.

In case $R^2$ and/or $R^3$ is an amino-substituted alkyl group in the case (E) where $R^8$ and $R^9$ are hydrogen atoms, a water-soluble ammonium salt can be formed at the nitrogen atom of the amino group with an inorganic or organic acid. In general, inorganic acids and organic acids capable of forming a water-soluble salt with a camptothecin derivative having an amino group are physiologically acceptable and are selected, for example, from hydrochloric acid, hydrobromic acid, hydroiodic acid, sulfuric acid, phosphoric acid, nitric acid, acetic acid, propionic acid, l-ascorbic acid, tartaric acid, citric acid, lactic acid, maleic acid, fumaric acid, methanesulfonic acid, toluenesulfonic acid and benzenesulfonic acid.

On the other hand, when $R^2$ and/or $R^3$ is an alkyl group substituted by an acid function in the case (C) such as carboxylic acid, sulfonic acid or phosphonic acid group or an ester form thereof, the acid function can be converted into an alkali metal salt form by the treatment with an alkali metal hydroxide or carbonate such as sodium hydroxide or carbonate, or potassium hydroxide or carbonate.

The E-ring structure of the camptothecin derivatives of this invention is not damaged by the formation of the above water-soluble salts. Thus, the pharmacological activities of the camptothecin derivatives are never affected by conversion to their water-soluble salts. It is believed that the camptothecin derivatives are easily converted to their 9-, 10- or 11-hydroxy (free) form in vivo by the action of a carboxyamidase or the like enzyme.

The 9-, 10- or 11-substituted new camptothecin derivatives of the present invention represented by the general formula (I) possess strong anti-tumor activity with reduced toxicity. Illustrative of the new camptothecin derivatives of the present invention are, for example, 9-chlorocarbonyloxycamptothecin (9-chlorocarbonyloxy-CPT; "camptothecin" will be referred to hereinafter simply as "CPT"), 9-chlorocarbonyloxy-7-ethyl-CPT, 10-chlorocarbonyloxy-CPT, 10-chlorocarbonyloxy-7-ethyl-CPT, 11-chlorocarbonyloxy-CPT, 11-chlorocarbonyloxy-7-ethyl-CPT, 7-ethyl-9-[4-(N-isopropylcarbamoylmethyl)-1-piperazino]carbonyloxy-CPT, 9-(1-piperazino)carbonyloxy-CPT, 9-(4-methyl-1-piperazino)carbonyloxy-CPT, 9-[4-(N-isopropylcarbamoylmethyl)-1-piperazino]carbonyloxy-CPT, 9-[4-(1-piperidino)-1-piperidino]carbonyloxy-CPT, 9-[N-methyl-N-(2-dimethylaminoethyl)]carbonyloxy-CPT, 7-ethyl-9-(1-piperazino)carbonyloxy-CPT, 7-ethyl-9-(4-methyl-1-piperazino)carbonyloxy-CPT, 7-ethyl-9-[4-(N-isopropylcarbamoylmethyl)-1-piperazino]carbonyloxy-CPT, 7-ethyl-9[4-(1-piperidino)-1-piperidino]carbonyloxy-CPT, 7-ethyl-9-[N-propyl-N-(2-dimethylaminoethyl)]carbonyloxy-CPT, 9-(1-piperazino)carbonyloxy-7-propyl-CPT, 10-[(N-ethoxycarbonylmethylamino)carbonyloxy]-7-ethyl-CPT, 10-(2-diethylamino)-ethyl-aminocarbonyloxy-7-ethyl-CPT, 10-diethylaminocarbonyloxy-7-ethyl-CPT, 7-ethyl-10-(4-morpholino)carbonyloxy-CPT, 7-ethyl-10-(1-piperazino)carbonyloxy-CPT, 7-ethyl-10-(4-methyl-1-piperazino)carbonyloxy-CPT, 7-ethyl-10-(4-ethyl-1-piperazino)carbonyloxy-CPT, 10-(4-benzyl-1-piperazino)carbonyloxy-7-ethyl-CPT, 7-ethyl-10-[4-(p-methoxyphenyl)-1-piperazino]carbonyloxy-CPT, 7-ethyl-10-[4-(3-hydroxypropyl)-1-piperazino]carbonyloxy-CPT, 7-ethyl-10-[4-(N-isopropylcarbamoylmethyl)-1-piperazino]carbonyloxy-CPT, 7-ethyl-10-[4-(1-piperidino)piperidino]carbonyloxy-CPT, 7-ethyl-10-[N-methyl-N-(2-dimethylaminoethyl)]aminocarbonyloxy-CPT, 7-ethyl-10-N-methyl-N-(1-methyl-4-piperidino)aminocarbonyloxy-CPT, 10-(4-morpholino)-carbonyloxy-CPT, 10-(4-methyl-1-piperazino)carbonyloxy-CPT, 7-ethyl-10-(4-propyl-1-piperazino)carbonyloxy-CPT, 7-ethyl-10-(4-methyl-1-piperazino)carbonyloxy-CPT, 11-(4-ethyl-1-piperazino)carbonyloxy-CPT, 11-[4-(1-piperidino)-1-piperidino]carbonyloxy-CPT, 11-(1-piperazino)carbonyloxy-CPT, 11-(4-methyl-1-piperazino)carbonyloxy-CPT, 11-[4-(N-isopropylcarbamoylmethyl)-1-piperazino]carbonyloxy-CPT, 11-[N-methyl-N-(2-dimethylaminoethyl)]carbonyloxy-CPT, 7-ethyl-11-(1-piperazino)carbonyloxy-CPT, 7-ethyl-11-(4-methyl-1-piperazino)carbonyloxy-CPT, 7-ethyl-11-[4-(N-isopropylcarbamoylmethyl)-1-piperazino]carbonyloxy-CPT, 7-ethyl-11-[N-methyl-N-(2-dimethylaminoethyl)]carbonyloxy-CPT and 7-ethyl-11-[4-(1-piperidino)-1-piperidino]carbonyloxy-CPT.

In accordance with the present invention, there is also provided a process for the preparation of the 9-, 10- or 11-substituted new camptothecin derivatives of the general formula (I).

The process of this invention wherein 9-, 10- or 11-hydroxy-7-$R^1$-camptothecin is used as starting material comprises two embodiments; one being directed to the reaction with phosgene optionally followed by amination with an amine to prepare both 9-, 10- or 11-chlorocarbonyloxy or aminocarbonyloxy compounds and the other being directed to the reaction with a carbamoyl chloride to exclusively obtain the corresponding 9-, 10- or 11-aminocarbonyloxy compounds.

In one embodiment of the process, the new camptothecin derivatives of the general formula (I) as well as ammonium salts or alkali metal salts thereof can be prepared by reacting a hydroxycamptothecin derivative of the general formula:

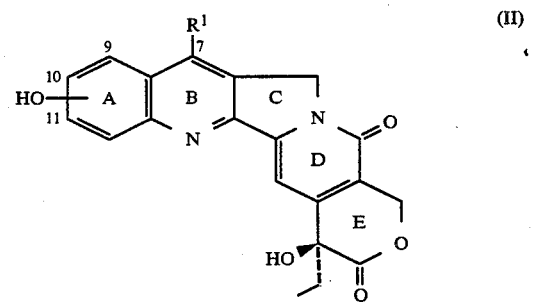

wherein $R^1$ is a hydrogen atom, a halogen atom or an alkyl group with 1-4 carbon atoms and the hydroxy group OH is bonded to a carbon atom located in any of the 9-, 10- and 11-positions in the ring A of camptothecin, with phosgene to form a chlorocarbonyloxycamptothecin derivative of the general formula:

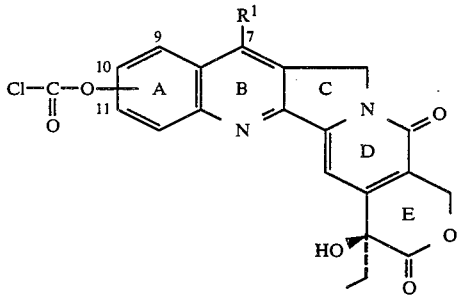

wherein $R^1$ has the same meaning as given above and the grouping Cl—CO—O— is bonded to a carbon atom located in any of the 9-, 10- and 11- positions in the ring A of camptothecin, and if necessary, treating the chlorocarbonyloxycamptothecin derivative (III) with an amine of the general formula:

wherein $R^2$ and $R^3$ are the same or different and each represents a hydrogen atom, a substituted or unsubstituted alkyl group with 1–4 carbon atoms or a substituted or unsubstituted carbocyclic or heterocyclic group with the proviso that when both $R^2$ and $R^3$ are the substituted or unsubstituted alkyl groups, they may be combined together with the nitrogen atom, to which $R^2$ and $R^3$ are bonded, to form a heterocyclic ring which may be interrupted with —O—, —S— and >N—$R^4$ in which $R^4$ is a hydrogen atom, a substituted or unsubstituted alkyl group with 1–4 carbon atoms or a substituted or unsubstituted phenyl group, and if desired, converting $R^2$ and/or $R^3$ in the resultant aminocarbonyloxycamptothecin derivative of the general formula (I) where X is

into another $R^2$ and /or $R^3$ by N-alkylation or O-alkylation according to the method known per se and/or converting the resultant aminocarbonyloxycamptothecin derivative into an ammonium salt thereof with an acid or into an alkali metal salt thereof with an alkali metal base.

The hydroxycamptothecin derivatives of the general formula (II) used as the starting material are known or can be prepared according to the known prior art processes. In case of 9-hydroxycamptothecin derivatives, i.e. the hydroxycamptothecin derivatives of the general formula (II) wherein the hydroxyl group —OH is located in the 9-position camptothecin is first treated carefully with nitric acid under ice-cooling to introduce a nitro group into the 9-position of camptothecin and the resultant 9-nitrocamptothecin is then treated with a reducing agent such as a combination of tin or iron with a mineral acid or is hydrogenated catalytically to form 9-aminocamptothecin. This 9-amino derivative is then treated in an acidic solution with a nitrite to form the corresponding diazonium compound which is then hydrolyzed to 9-hydroxycamptothecin (Japanese Laid-open Patent Appln. No. 59-51289). If necessary, this hydroxy derivative is alkylated in the 7-position (U.S. Pat. No. 4,399,282) or halogenated in the 7-position via N-oxidation. In case of 10-hydroxycamptothecin derivatives, i.e. the hydroxycamptothecin derivatives of the general formula (II) wherein the hydroxyl group —OH is located in the 10-position, a 7-$R^1$-camptothecin is treated in a liquid vehicle such as acetic acid with a peroxide to form the corresponding N-oxide which is then irradiated with actinic light in the presence of a solvent or a solvent mixture selected from methyl cellosolve, dioxane, acetonitrile, chloroform, methylene chloride, glyme and diglyme and in the presence of a mineral acid such as sulfuric acid or perchloric acid or an organic sulfonic acid (Japanese Laid-open Patent Appln. No. 58-39685; U.S. Ser. No. 414,528). In case of 11-hydroxycamptothecin derivatives, i.e. the hydroxycamptothecin derivatives of the general formula (II) wherein the hydroxyl group —OH is located in 11-position, camptothecin is subjected to catalytic hydrogenation to form 1,2,6,7-tetrahydrocamptothecin (the ring-B-hydrogenated derivative) which is then subjected to a series of reactions, i.e. nitration and simultaneous dehydrogenation in the presence of concentrated sulfuric acid, reduction of the resultant 11-nitrocamptothecin to the corresponding 11-amino derivative, the subsequent diazotization to the corresponding diazonium salt, and hydrolysis of the diazonium salt by warming (Japanese Laid-open Patent Appln. No. 59-51287). If necessary, the resultant 11-hydroxycamptothecin is subjected to 7-alkylation or to 7-halogenation.

Primary and secondary amines of the general formula (IV) are known and easily commercially available. When $R^2$, $R^3$ and $R^4$ are substituted alkyl groups, the substituents are selected from the aforesaid cases (A)–(F). When the phenyl group is substituted, the substituent or substituents correspond to $R^7$ in the case (D). The carbocyclic and heterocyclic groups are selected usually from cycloalkyl, phenyl and saturated or aromatic heterocyclic groups and the substituents are selected from halogen atoms, alkyl groups with 1–4 carbon atoms and alkoxy groups with 1–4 carbon atoms. Accordingly, a wide variety of amines can be used as the reactant $HNR^2R^3$. Illustrative of the amine are, for example, ammonia, a primary $C_{1-4}$ alkylamine such as methylamine or ethylamine, a secondary $C_{1-4}$ dialkylamine such as dimethylamine or diethylamine, a halogen-substituted primary or secondary alkylamine such as 2-chloroethylamine, a hydroxy- or alkoxy-substituted amine such as 2-hydroxyethylamine or 2,2'-dimethoxydiethylamine, an amine having an acid function such as ethoxycarbonylmethylamine or ethoxysulfonylethylamine, a phenylalkylamine such as benzylamine, 4-methoxyphenylpropylamine or 2,4-dichlorophenethylamine, an aminoalkylamine such as 2-(N,N-diethylamino)ethylamine, an aminocarbonylalkylamine such as isopropylaminocarbonylethylamine or dimethylaminoethylmethylamine, a heterocyclic amine such as morpholine, piperidine, piperazine, N-benzylpiperazine, 1-methylpiperazine, 4-(1-piperidino)piperidine or 4-(4-methoxyphenyl)piperazine, an esterified alkylamine such as methoxyethoxycarbonylmethylamine, dimethylaminoethoxycarbonylmethylamine or methoxycarbonylethylcarbonyloxypropylamine, and other cyclic amine such as N-methyl-4-piperidylmethylamine.

In the first step of the process, a hydroxycamptothecin of the general formula (II) is dissolved in an anhydrous solvent and gaseous phosgene is introduced into the solution under agitation at a temperature in a wide range, preferably at room temperature. Preferable examples of the solvent for the hydroxycamptothecin include dioxane, acetone, chloroform, methylene chloride, methanol, ethanol and a mixture of these solvents. The gaseous phosgene is usually employed in a slightly excess amount. The condensation reaction of the hydroxycamptothecin with phosgene proceeds while splitting off hydrogen chloride. Thus, the reaction can be promoted rapidly by addition of an acid-binding agent to the reaction system. A tertiary amine such as triethylamine, pyridine, picoline, 1,8-diazabicyclo[5.4.-0]undec-7-en (DBU), 1,5-diazabicyclo[4.3.0]non-5-ene (DBN) or trimethylamine, an alkali metal hydride such as sodium hydride, and an alcoholate such as sodium ethoxide or potassium tert-butoxide are suitable acid-binding agents in this case and are usually employed in a slightly excess amount. The end point of the reaction is confirmed by complete consumption of the starting material. For this purpose, a trace amount of the reaction mixture is sampled and subjected to TLC or the like analysis to detect the starting material. The reaction is finished usually within one hour. After completion of the reaction, any insoluble matter is removed by filtration and the filtrate is allowed to evaporate under reduced pressure until dryness whereby a chlorocarbonyloxycamptothecin of the general formula (III) is obtained quantitatively as a light yellowish white powdery substance.

In the second step of the process, a chlorocarbonyloxycamptothecin of the general formula (III) is suspended in a solvent and an amine of the general formula (IV) is then added to the suspension under agitation. The reaction is conducted under warming or at room temperature. The solvent used in this second step is usually identical with that used in the first step. This amination reaction proceeds with the liberation of hydrogen chloride. Thus, the reaction can be promoted by using an acid-binding agent as in the first step. In this amination reaction, therefore, the amine is used in an excess amount, a part of which functions as an acid-binding agent to capture the liberated hydrogen chloride thereby promoting the reaction. It is a matter of course that a tertiary amine or a metal compound as exemplified in the first step can be used as an acid-binding agent. In this case, the amount of the amine to be reacted with the compound of the general formula (III) can be reduced. A part of the reaction mixture is occasionally sampled and analyzed to confirm whether the starting material has entirely been consumed or not. The reaction is finished usually within 36 hours at room temperature but the reaction time can be shortened by warming the reaction mixture to accelerate the reaction. After completion of the reaction, the solvent is distilled off under reduced pressure and the residue is then extracted with a solvent such as dioxane. The solvent is removed from the extract and the residue is then subjected to separation and purification by way of column chromatography or T.L.C. on silica gel. Various aminocarbonyloxycamptothecin derivatives (X is —NR²R³ is in the general formula I) can thus be obtained.

In another embodiment of the process of this invention, such aminocarbonyloxycamptothecin derivatives of the general formula:

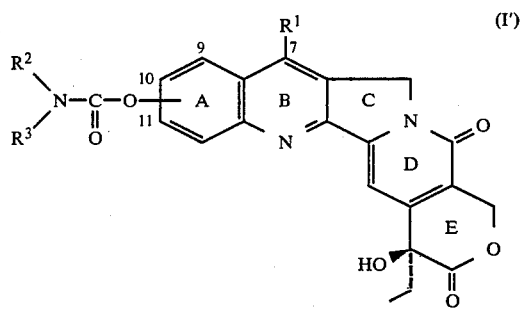

(I')

wherein $R^1$, $R^2$ and $R^3$ have the same meanings as given above and wherein the grouping $R^2R^3N$—CO—O— is bonded to a carbon atom in any of the 9-, 10- and 11-positions thereof, as well as ammonium salts or alkali metal salts thereof, can be prepared by reacting a hydroxycamptothecin of the general formula (II) with a carbamoyl chloride of the general formula (V):

Cl—CO—NR²R³        (V)

wherein $R^2$ and $R^3$ have the same meanings as given above, in a liquid vehicle preferably in the presence of an acid-binding agent, and if desired, converting $R^2$ and/or $R^3$ in the resultant aminocarbonyloxycamptothecin derivative of the general formula (I') into another $R^2$ and/or $R^3$ by N-alkylation or O-alkylation according to the method known per se and/or converting the resultant aminocarbonyloxycamptothecin derivative into an ammonium salt thereof with an acid or into an alkali metal salt thereof with an alkali metal base.

Carbamoyl chlorides of the general formula (V) can be prepared in a high purity and in a high yield according to the method known per se by reacting an amine of the general formula (IV) in a solvent with phosgen or phosgen dimer. Examples of the solvent used in this case include non-polar inert solvents such as benzene, toluene or the like aromatic hydrocarbon and hexane or the like aliphatic hydrocarbons.

The reaction between the hydroxycamptothecin derivative of the general formula (II) and the carbamoyl chloride of the general formula (V) is carried out by usually using the latter in an excess amount (1.2–2.0 times as much as the theoretical amount) at room temperature or under warming. When the carbamoyl chloride is used in an amount more than 1.8 times of the theoretical amount, the reaction will be finished within a short period of time at room temperature. Illustrative of the liquid vehicle used for this reaction are, for example, polar aprotic solvents such as dimethylformamide, diethylformamide, dimethylsulfoxide, hexamethylphosphoramide and pyridine. Preferable examples of the acid-binding agent include a metal hydride such as sodium hydride, a metal alcoholate such as potassium tert-butoxide, and a tertiary amine such as triethylamine, 4-(N,N-dimethylamino)pyridine, pyridine, picoline, lutidine, collidine, DBU and DBN. The use of pyridine is preferable because it is good for dual purposes of solvent and acid-binding agent. These tertiary amines may be used in an excess amount for dual purpose as the solvent and the acid-binding agent. The reaction is usually finished within 20 hours and within 2 hours in a preferable case.

The aminocarbonyloxycamptothecin derivatives of this invention thus obtained can further be treated with a reagent for converting $R^2$ and/or $R^3$ into another $R^2$ and/or $R^3$. In case $R^2$ and/or $R^3$ is a hydrogen atom or an alkyl group carrying as substituent OH or $-NR^8R^9$ where at least one of $R^8$ and $R^9$ is a hydrogen atom or in case $R^2$ and $R^3$ are combined together with the nitrogen atom, to which they are bonded, to form a heterocyclic ring interrupted with $>N-R^4$ where $R^4$ is a hydrogen atom, such hydrogen atom can be converted into an alkyl group by N- or O-alkylation according to the method known per se for N-alkylation or O-alkylation. An alkyl halide with 1-4 carbon atoms such as methyl iodide, ethyl bromide or propyl bromide, a dialkyl sulfate with 1-4 carbon atoms in each alkyl moiety such as dimethyl sulfate or diethylsulfate, a diazoalkane with 1-4 carbon atoms such as diazomethane and the like alkylating agents come into question as the alkylating agents for this purpose. For example, 10-(2-aminoethylmethyl)aminocarbonyloxycamptothecin can be treated with ethyl bromide to form the corresponding 10-(2-diethylaminoethylmethyl)aminocarbonyloxy derivative and 10-piperazinocarbonyloxycamptothecin can be treated with propyl bromide to form the corresponding 10-(4-propyl-1-piperazino)carbonyloxy derivative.

The new camptothecin derivative of the general formula (I) wherein $R^2$ and/or $R^3$ has an amino group or of the general formula (I') can be treated, if desired, with a stoichiometrical amount of an acid such as hydrochloric acid, p-toluenesulfonic acid, acetic acid, tartaric acid, maleic acid or fumaric acid to form a water-soluble ammonium salt of the camptothecin derivative. On the other hand, the camptothecin derivative wherein $R^2$ and/or $R^3$ has an acid function such as carboxyl group or an alkoxycarbonyl group can be treated, if desired, with a stoichiometrical amount of a strong alkali metal base such as sodium hydroxide, potassium hydroxide or the like to form a water-soluble alkali metal salt.

The water-soluble ammonium salts or alkali metal carboxylates can be converted, if necessary, into the free form by treating the salts with an alkaline substance such as sodium hydroxide or sodium carbonate or treating the carboxylates with a strong or weak acid such as hydrochloric acid or acetic acid, respectively.

The process starting with the compound of the general formula (II) is convenient for preparing a wide variety of the aminocarbonyloxycamptothecin derivatives, while the process starting with the compound of the general formula (V) is convient for preparing a particular end product in a large amount.

The chlorocarbonyloxy- and aminocarbonyloxycamptothecin derivatives of the present invention represented by the general formula (I) can be used as such or after further purification as active ingredients for anti-tumor medicaments or as valuable intermediate products for preparing other useful products. Accordingly, the present invention is of particular significance in developing 9-, 10- or 11-substituted camptothecin derivatives as a new class of camptothecin derivatives useful as anti-tumor medicaments possessing strong anti-tumor activity with reduced toxicity and also as intermediate products for preparing other useful new products as well as a new process for preparing these valuable camptothecin derivatives in a simple economically advantageous operation.

The present invention will now be illustrated in more detail by way of examples.

EXAMPLE 1

9-Chlorocarbonyloxy-7-propylcamptothecin

A suspension of 9-hydroxy-7-propylcamptothecin (100 mg, 0.246 mmol) in dry dioxane (150 ml) containing 400 μl of trimethylamine was warmed gently until the hydroxylic compound was dissolved in the dioxane. After cooling the solution to room temperature, phosgene gas freshly prepared by decomposition of trichloromethoxy chloroformate (100 μl) on charcoal was passed through the solution with stirring, and then the mixture was stirred for 30 min. at room temperature. After confirming that the starting material had disappeared completely by way of TLC (10% MeOH-$CHCl_3$, 365 nm), the precipitated material was filtered off by suction and the filtrate was evaporated to dryness in vacuo. The residual colorless powder was washed with a small amount of dry dioxane, filtered, and then dried in vacuo. The title compound was obtained in 94% yield (108 mg) as colorless powder.

IR $\nu KBr/max$ cm$^{-1}$: 2970, 2920, 1770, 1655, 1590, 1500, 1220, 1170.

EXAMPLE 2

9-[4-(Isopropylcarbamoylmethyl)-1-piperazino]carbonyloxycamptothecin

9-Hydroxycamptothecin (190 mg, 0.521 mmol) and 1-chlorocarbonyl-4-(isopropylcarbamoylmethyl)piperazine (257 mg, 1.04 mmol) were dissolved in anhydrous pyridine (12 ml) and the mixture was stirred for 4.5 hours at room temperature. The reaction mixture was evaporated to dryness in vacuo and the residue was dissolved in $CHCl_3$ (100 ml). The $CHCl_3$ solution was shaken with a 7% aqueous solution of $NaHCO_3$ (100 ml), washed with a saturated aqueous solution of NaCl, dried with $MgSO_4$, filtered, and then evaporated to dryness in vacuo. The residual material was purified through silica gel column chromatography with 2% MeOH-$CHCl_3$ as an eluent to give 290 mg (96.9% yield) of the title compound, which was then recrystallized from ethanol to give 160 mg of pale yellow needles.

$^1$H-NMR (DMSO-$d_6$) δppm: 0.84 (3H, t, J=7 Hz), 1.10 (6H, d, J=6 Hz), 2.84 (2H, q, J=7 Hz), 2.45–2.80 (5H, m), 3.04 (2H, s), 3.40–4.00 (4H, br), 5.32 (2H, s), 6.50 (1H, s, $D_2O$-exchangeable), 7.40–8.10 (4H, m), 8.56 (1H, s).

EXAMPLE 3

7-Methyl-9-[4-(isopropylcarbamoylmethyl)-1-piperazino]carbonyloxycamptothecin

To a solution of 9-hydroxy-7-methylcamptothecin (100 mg, 0.264 mmol) in pyridine (5 ml) was added 1-chlorocarbonyl-4-(isopropylcarbamoylmethyl)piperazine (120 mg, 0.5 mmol). The mixture was stirred for 18 hours at room temperature. The reaction mixture was evaporated to dryness in vacuo and the residual material was shaken with a mixture of $CHCl_3$ (300 ml) and a 7% aqueous solution of $NaHCO_3$ (300 ml). The $CHCl_3$ phase was separated, washed with a saturated aqueous solution of NaCl (300 ml), dried with anhydrous $MgSO_4$, filtered, and then evaporated to dryness in vacuo. The residual material was purified through silica gel column chromatography with 2%-MeOH-$CHCl_3$ as an eluent to give a pale yellow mass, which was then recrystallized from ethanol whereby 93 mg (65% in yield) of the title compound was obtained as pale yellow needles.

EXAMPLE 4

7-Ethyl-9-[4-(1-piperidino)piperidino]carbonyloxycamptothecin (A) 9-Methoxycamptothecin (300 mg, 0.79 mmol) was suspended in water (6 ml) Conc. $H_2SO_4$ (3 ml) was added dropwise to the suspension until the methoxycamptothecin was dissolved therein. After cooling the solution in an ice-bath, propionaldehyde (0.13 ml, 1.6 mmol) and $FeSO_4.7H_2O$ (60 mg, 0.215 mmol) were added to the solution, and 30% $H_2O_2$ (0.35 ml, 2.77 mmol) was then added dropwise to the mixture with stirring under cooling in an ice-bath. After addition of the hydrogen peroxide, the reaction mixture was continuously stirred for 30 minutes at room temperature. The resulting mixture was poured into ice-water (1 l), and the precipitate in the solution was extracted with $CHCl_3$. The $CHCl_3$ layer was washed with water, dried with $MgSO_4$, filtered, and then evaporated to dryness in vacuo. The residue was recrystallized from EtOH to give 256 mg (79.8% in yield) of 7-ethyl-9-methoxycamptothecin as pale yellow needles.

M.P. 274°–276° C. (dec.) [EtOH].

$^1$H-NMR (in $CDCl_3$) δppm: 1.02 (3H, t, J=8 Hz), 1.33 (3H, t, J=7 Hz), 1.92 (2H, q, J=8 Hz), 3.06–3.77 (2H, m), 4.03 (3H,s), 5.07 (2H,s), 5.28 (1H, d, J=17 Hz), 5.67 (1H, d, J=17 Hz), 6.87–7.10 (1H, m), 7.20–7.83 (3H, m).

MS m/e: 406 [M+].

Elementary analysis as $C_{23}H_{16}N_2O_5$: Calcd. C, 67.97; H, 5.46; N, 6.89; Found C, 67.79; H, 5.38; N, 6.82.

(B) The 7-ethyl-9-methoxycamptothecin (250 mg, 0.62 mmol) thus obtained was dissolved in 47% HBr (5 ml) and the solution was heated at 140° C. for 8 hours with stirring. The mixture was poured into ice-water (1 l) and the precipitated material was collected on a filter by suction. The solid material collected was recrystallized from EtOH whereby 100 mg (44% in yield) of 7-ethyl-9-hydroxycamptothecin was obtained as pale yellow needles.

M.P. 270°–272° C. (dec.) [EtOH].

MS m/e: 392 [M+].

Elementary analysis as $C_{22}H_{20}N_2O_5$: Calcd. C, 67.33; H, 5.14; N, 7.14; Found C, 67.13; H, 5.10; N, 7.33.

(C) 7-Ethyl-9-hydroxycamptothecin (100 mg, 0.27 mmol) obtained in (B) was dissolved in dry pyridine (6 ml). To the solution was added 1-chlorocarbonyloxy-4-piperidinopiperidine (200 mg, 0.87 mmol), and the mixture was stirred for one hour at room temperature. The reaction mixture was evaporated to dryness in vacuo and the residue was purified by way of column chromatography on silica gel with 2%-MeOH-$CHCl_3$ as an eluent whereby the title compound was obtained as a pale yellow solid, which was then recrystallized from EtOH to give 80 mg (50% in yield) of the title compound as pale yellow needles.

M.P. 210°–212° C. (dec.) [EtOH].

$^1$H-NMR (in $CDCl_3$) δppm: 1.00 (3H, t, J=8 Hz), 1.17–2.20 (15H, m), 2.20–2.77 (5H, m), 2.77–3.30 (4H, m), 4.20–4.67 (2H, br), 5.20 (2H, s), 5.22 (1H, d, 16 Hz), 5.70 (1H, d, J=16 Hz), 7.40–7.62 (1H, m), 7.62–8.10 (4H, m).

Elementary analysis as $C_{33}H_{38}N_4O_6 \cdot H_2O$: Calcd. C, 65.54; H, 6.67; N, 9.27; Found C, 65.34; H, 6.50; N, 9.50.

EXAMPLE 5

9-(1-piperazino)carbonyloxy-7-propylcamptothecin (A) 9-Methoxycamptothecin (1.00 g, 2.65 mmol) was suspended in water (20 ml). To the solution, Conc. $H_2SO_4$ (ca 10 ml) was added until the methoxycamptothecin was dissolved in the mixture.

After cooling the solution in an ice-bath, butyrylaldehyde (0.5 ml, 5.2 mmol) and $FeSO_4.7H_2O$ (200 mg, 0.7 mmol) were added to the solution, and 30% $H_2O_2$ (1.25 ml, 9.3 mmol) was then added dropwise to the mixture under agitation and cooling in an ice-bath. After additional agitation for 12 hours at room temperature, the reaction mixture was poured into ice-water (1 l) and the precipitated formed in the solution was extracted with $CHCl_3$. The $CHCl_3$ layer was separated, washed with water, dried with $MgSO_4$, filtered, and then evaporated to dryness in vacuo. The residue was recrystallized from EtOH whereby 520 mg (46.7% in yield) of 9-methoxy-7-propylcamptothecin was obtained as pale yellow needles.

M.P. 276°–278° C. (dec.) [EtOH].

MS m/e: 420 [M+].

Elementary analysis as $C_{24}H_{24}N_2O_5$: Calcd. C, 68.56; H, 5.75; N, 6.66; Found C, 68.46; H, 5.70; N, 6.80.

9-Methoxy-7-propylcamptothecin (500 mg, 1.2 mmol) was dissolved in 47% HBr (5 ml) and the solution was heated at 140° C. for 8 hours with stirring. The mixture was poured into ice-water (1 l) and the precipitated material was collected on a filter by suction and the collected material was recrystallized from EtOH to give 200 mg (41.1% in yield) of 9-hydroxy-7-propylcamptothecin as pale yellow needles.

M.P. 280° C.

Elementary analysis as $C_{23}H_{22}N_2O_5$: Calcd. C, 67.96; H, 5.46; N, 6.89; Found C, 67.77; H, 5.30; N, 6.99.

(B) 9-Hydroxy-7-propylcamptothecin (220 mg, 0.54 mmol) is dissolved in dry dioxane (500 ml) containing 0.3 ml of triethylamine. Phosgen gas (phosgen dimer 0.1 ml, 1.6 mmol) is introduced into the solution under stirring at room temperature. After additional stirring for 3 hours at room temperature, the precipitated material is removed by filtration and the filtrate is evaporated to dryness in vacuo. The residue (9-chlorocarbonyloxy-7-propylcamptothecin) is dissolved in 20% methanol-chloroform (100 ml) containing 0.3 ml of triethylamine. To the mixture is added anhydrous piperazine (51 mg, 0.65 mmol), and the mixture is stirred for 18 hours at room temperature. The reaction mixture is then worked up in the same manner as described in Example 4(C) and the resultant crude product is purified by way of column chromatography on silica gel followed by recrystallization from ethanol whereby 28 mg (10% in yield) of the title compound is obtained as pale yellow needles.

EXAMPLE 6

10-Chlorocarbonyloxy-7-ethylcamptothecin

7-Ethyl-10-hydroxycamptothecin (500 mg, 1.27 mmol) was suspended in dry dioxane (400 ml) and dissolved therein by adding triethylamine (2 ml) to the suspension under warming. This solution was stirred at room temperature while introducing thereinto phosgene prepared toties quoties by decomposing phosgene dimer (trichloromethoxychloroformate, 400 μl) in the presence of an active carbon catalyst. After 0.5 hours, consumption of the starting materials was confirmed and insoluble matters were then removed by filtration. The solvent was distilled off under reduced pressure whereby the title compound was obtained as white powders (565 mg, 97.4%).

IR $\nu_{max}^{KBr}$cm$^{-1}$: 3430, 2980, 2940, 1775, 1744, 1656, 1595, 1514, 1458, 1222, 1161, 1033, 721.

EXAMPLE 7

10-Chlorocarbonyloxycamptothecin

10-Hydroxycamptothecin (700 mg, 1.92 mmol) was suspended in dry dioxane (1000 ml) and dissolved therein by adding triethylamine (2.5 ml) to the suspension under warming. The solution was stirred at room temperature while introducing thereto phosgene prepared toties quoties by decomposing phosgene dimer (trichloromethoxychloroformate, 500 μl) in the presence of an active carbon catalyst. After 0.5 hour, consumption of the starting materials was confirmed and insoluble matters were then removed by filtration. The solvent was distilled off under reduced pressure whereby the title compound was obtained as white powders (800 mg, 97.5%).

IR $\nu_{max}^{KBr}$cm$^{-1}$: 3450, 2970, 2930, 1775, 1740, 1665, 1590, 1502, 1222, 1186, 1045, 828.

Shown in the following Examples 8–23 is a general process for synthesizing various 10-aminocarbonyloxy-7-ethylcamptothecin compounds which comprises the steps as will be shown below.

10-Chlorocarbonyloxy-7-ethylcamptothecin (300 mg, 0.66 mmol) is suspended in dry dioxane (50 ml). To this suspension is added an amine described in each Example and the mixture is stirred under a warming or non-warming condition until the starting materials are consumed. The solvent is then removed by distillation under reduced pressure and the residue is subjected to separation and purification by the aid of column chromatography on silica gel whereby a 10-aminocarbonyloxy-7-ethylcamptothecin mentioned as a title compound of each Example is obtained.

In each Example are also given the yield of a compound obtained and characteristic physical data of the compound.

EXAMPLE 8

10-[(N-ethoxycarbonylmethylamino)carbonyloxy]-7-ethylcamptothecin

Using glycine ethyl ester (350 mg, 3.40 mmol) as the amine, the reaction followed by the after-treatment was carried out whereby the title compound (65 mg, 18.9%) was obtained.

M.P. 135°–138° C. (dec.).

$^1$H-NMR (in CDCl$_3$) δppm: 0.93 (3H, t, J=7 Hz), 1.19 (6H, t, J=7 Hz), 1.81 (2H, q, J=7 Hz), 3.00 (2H, q, J=7 Hz), 4.00–4.32 (4H, m), 5.08 (2H, s), 5.41 (2H, ABq.), 7.50 (1H, s), 7.39–8.10 (3H, m).

EXAMPLE 9

10-(2-diethylamino)ethylaminocarbonyloxy-7-ethylcamptothecin

Using N,N-diethylethylenediamine (380 mg, 3.30 mmol) as the amine, the reaction followed by the after-treatment was carried out whereby the title compound (229 mg, 65.0%) was obtained.

M.P. 154°–157° C. (dec.).

EXAMPLE 10

10-diethylaminocarbonyloxy-7-ethylcamptothecin

Using diethylamine (150 mg, 2.05 mmol) as the amine, the reaction followed by the after-treatment was carried out whereby the title compound (210 mg, 64.8%) was obtained.

M.P. 239°–242° C. (dec.).

$^1$H-NMR (in CDCl$_3$) δppm: 1.03 (3H, t, J=7 Hz), 1.25 (3H, t, J=7 Hz), 1.39 (6H, t, J=7 Hz), 1.84 (2H, q, J=7 Hz), 3.11 (2H, q, J=7 Hz), 3.44 (4H, ps. quint.), 5.16 (2H, s), 5.42 (2H, ABq.), 7.45 (1H, dxd, J=2 Hz, 8 Hz), 7.50 (1H, s), 7.71 (1H, d, J=2 Hz), 8.06 (1H, d, J=8 Hz).

IR $\nu_{max}^{KBr}$cm$^{-1}$: 3480, 3040, 3010, 1763, 1735, 1674, 1615, 1428, 1285, 1246, 1205, 1172, 1000, 860.

EXAMPLE 11

7-Ethyl-10-(4-morpholino)carbonyloxycamptothecin

Using morpholine (180 mg, 2.06 mmol) as the amine, the reaction followed by the after-treatment was carried out whereby the title compound (230 mg, 69.0%) was obtained.

M.P. 245°–248° C. (dec.).

$^1$H-NMR (in CDCl$_3$) δppm: 1.03 (3H, t, J=7 Hz), 1.41 (3H, t, J=7 Hz), 1.90 (2H, q, J=7 Hz), 3.16 (2H, q, J=7 Hz), 3.70–3.80 (8H, m), 5.25 (2H, s), 5.51 (2H, ABq.), 7.58 (1H, dxd, J=2 Hz, 8 Hz), 7.65 (1H, s), 7.84 (1H, d, J=2 Hz), 8.23 (1H, d, J=8 Hz).

IR $\nu_{max}^{KBr}$cm$^{-1}$: 3440, 2970, 1715, 1655, 1603, 1412, 1226, 1185, 1160, 1116, 1054, 940.

EXAMPLE 12

7-Ethyl-10-(1-piperazino)carbonyloxycamptothecin

Using piperazine (300 mg, 3.48 mmol) as the amine, the reaction followed by the after-treatment was carried out whereby the title compound (85 mg, 25.5%) was obtained.

M.P. 228°–230° C. (dec.).

$^1$H-NMR (in DMSO-d$_6$) δppm: 0.90 (3H, t, J=7 Hz, 1.32 (3H, t, J=7 Hz), 1.97 (2H, q, J=7 Hz), 3.04–3.65 (10H, m), 5.32 (2H, s), 5.44 (2H, s), 6.50 (1H, s), 7.34 (1H, s), 7.66 (1H, dxd, J=2 Hz, 8 Hz), 7.97 (1H, d, J=2 Hz), 8.16 (1H, d, J=8 Hz).

IR $\nu_{max}^{KBr}$cm$^{-1}$: 3430, 2960, 2940, 1745, 1718, 1660, 1590, 1413, 1230, 1190, 1053, 840.

Elementary analysis as C$_{27}$H$_{28}$N$_4$O$_6$.H$_2$O: Calcd. C, 62.05; H, 5.79; N, 10.72; Found C, 62.02; H, 5.42; N, 10.96.

EXAMPLE 13

7-Ethyl-10-(4-methyl-1-piperazino)carbonyloxycamptothecin

Using N-methylpiperazine (200 mg, 2.02 mmol) as the amine, the reaction followed by the after-treatment was carried out whereby the title compound (185 mg, 54.2%) was obtained.

M.P. 236°–239° C. (dec.).

$^1$H-NMR (in DMSO-d$_6$) δppm: 0.88 (3H, t, J=7 Hz), 1.29 (3H, t, J=7 Hz), 1.87 (2H, q, J=7 Hz), 2.25 (3H, s), 3.18 (2H, q, J=7 Hz), 3.49–3.64 (8H, m), 5.31 (2H, s), 5.43 (2H, s), 6.50 (1H, s), 7.31 (1H, s), 7.64 (1H, dxd, J=2 Hz, 9 Hz), 7.97 (1H, d, J=2 Hz), 8.15 (1H, d, J=9 Hz).

IR $\nu_{max}^{KBr}$cm$^{-1}$: 3430, 2970, 2940, 1743, 1715, 1655, 1598, 1459, 1412, 1292, 1228, 1190, 1052, 1001, 841, 817.

Elementary analysis as $C_{30}H_{34}N_4O_7 \cdot \frac{1}{2}H_2O$: Calcd. C, 63.75; H, 5.92; N, 10.62 Found C, 63.87; H, 5.74; N, 10.71.

EXAMPLE 14

7-Ethyl-10-(4-ethyl-1-piperazino)carbonyloxycamptothecin

Using N-ethylpiperazine (230 mg, 2.03 mmol) as the amine, the reaction followed by the after-treatment was carried out whereby the title compound (264 mg, 75.3%) was obtained.

M.P. 200°-203° C. (dec.).

$^1$H-NMR (in DMSO-d$_6$) δppm: 0.90 (3H, t, J=7 Hz), 1.06 (3H, t, J=7 Hz), 1.32 (3H, t, J=7 Hz), 1.90 (2H, q, J=7 Hz), 2.42 (2H, q, J=7 Hz), 3.18-3.17 (10H, m), 5.33 (2H, s), 5.44 (2H, s), 6.48 (1H, s), 7.35 (1H, s), 7.66 (1H, dxd, J=2 Hz, 8 Hz), 7.99 (1H, d, J=2 Hz), 8.18 (1H, d, J=8 Hz).

IR $\nu_{max}^{KBr}$cm$^{-1}$: 3430, 2960, 2930, 1742, 1720, 1655, 1597, 1412, 1206, 1185, 1162, 817.

EXAMPLE 15

10-(4-Benzyl-1-piperazino)carbonyloxy-7-ethylcamptothecin

Using N-benzylpiperazine (290 mg, 1.65 mmol) as the amine, the reaction followed by the after-treatment was carried out whereby the title compound (320 mg, 81.8%) was obtained.

M.P. 160°-162° C. (dec.).

$^1$H-NMR (in DMSO-d$_6$) δppm: 0.89 (3H, t, J=7 Hz), 1.29 (3H, t, J=7 Hz), 1.87 (2H, q, J=7 Hz), 3.19 (2H, q, J=7 Hz), 3.56 (2H, s), 3.50-3.70 (8H, m), 5.32 (2H, s), 5.43 (2H, s), 6.50 (1H, s), 7.32 (1H, s), 7.34 (5H, s), 7.45 (1H, dxd, J=8 Hz, 2 Hz), 7.97 (1H, d, J=2 Hz), 8.16 (1H, d, J=8 Hz).

IR $\nu_{max}^{KBr}$cm$^{-1}$: 3440, 2940, 1720, 1655, 1600, 1415, 1226, 1183, 1055, 1000.

Elementary analysis as $C_{34}H_{34}N_4C_6 \cdot H_2O$: Calcd. C, 66.65; H, 5.92; N, 9.14; Found C, 67.13; H, 5.62; N, 9.37.

EXAMPLE 16

7-Ethyl-10-[4-(4-methoxyphenyl)-1-piperazino]carbonyloxycamptothecin

Using N-(4-methoxyphenyl)piperazine (380 mg, 1.98 mmol) as the amine, the reaction followed by the after-treatment was carried out whereby the title compound (255 mg, 63.3%) was M.P. 156°-158° C. (dec.).

$^1$H-NMR (in DMSO-d$_6$) δppm: 0.89 (3H, t, J=7 Hz), 1.30 (3H, t, J=7 Hz), 1.88 (2H, q, J=7 Hz), 3.14 (6H, br.s), 3.71 (3H, s), 3.72 (4H, br.s), 5.32 (2H, s), 5.44 (2H, s), 6.50 (1H, s), 6.91 (4H, ABq), 7.32 (1H, s), 7.69 (1H, dxd, J=2 Hz, 8 Hz), 8.01 (1H, d, J=2 Hz), 8.18 (1H, d, J=8 Hz).

IR $\nu_{max}^{KBr}$cm$^{-1}$: 3440, 2970, 2940, 1745, 1720, 1658, 1600, 1515, 1415, 1228, 1196, 1160, 1035, 825.

EXAMPLE 17

7-Ethyl-10-[4-(3-hydroxypropyl)-1-piperazino]carbonyloxycamptothecin

Using N-(3-hydroxypropyl)piperazine (300 mg, 2.08 mmol) as the amine, the reaction followed by the after-treatment was carried out whereby the title compound (180 mg, 48.5%) was obtained.

M.P. 228°-230° C. (dec.).

$^1$H-NMR (in DMSO-d$_6$) δppm: 0.89 (3H, t, J=3 Hz), 1.30 (3H, t, J=7 Hz), 1.63 (2H, m), 1.88 (2H, q, 7 Hz), 3.20-3.65 (14H, m), 5.32 (2H, s), 5.43 (2H, s), 6.51 (1H, s), 7.32 (1H, s), 7.65 (1H, dxd, J=2 Hz, 8 Hz), 7.98 (1H, d, J=2 Hz), 8.17 (1H, d, J=8 Hz).

IR $\nu_{max}^{KBr}$cm$^{-1}$: 3300, 2940, 1709, 1655, 1592, 1412, 1228, 1185, 1055, 815.

EXAMPLE 18

7-Ethyl-10-[4-(isopropylcarbamoylmethyl)-1-piperazino]carbonyloxycamptothecin

Using N-(isopropylcarbamoylmethyl)piperazine (370 mg, 2.00 mmol) as the amine, the reaction followed by the after-treatment was carried out whereby the title compound (133 mg, 33.4%) was obtained.

M.P. 237-240° C. (dec.).

$^1$H-NMR (in DMSO-d$_6$) δppm: 0.89 (3H, t, J=7 Hz), 1.09 (6H, d, J=6 Hz), 1.30 (3H, t, J=7 Hz), 1.88 (2H, q, J=7 Hz), 2.60 (4H, br.s), 3.23 (2H, s), 3.40-3.70 (4H, m), 3.70-4.00 (1H, m), 5.32 (2H, s), 5.43 (2H, s), 6.50 (1H, s), 7.32 (1H, s), 7.56 (1H, d, J=8 Hz), 7.65 (1H, dxd, J=2 Hz, 8 Hz), 7.98 (1H, d, J=2 Hz), 8.16 (1H, d, J=8 Hz).

IR $\nu_{max}^{KBr}$cm$^{-1}$: 3420, 3340, 2960, 1750, 1720, 1655, 1595, 1225, 1182, 1052.

Elementary analysis as $C_{32}H_{37}N_5O_7 \cdot H_2O$: Calcd. C, 61.88; H, 6.33; N, 11.28, Found C, 61.89; H, 6.33; N, 11.28.

EXAMPLE 19

7-Ethyl-10-[4-(1-piperidino)-1-piperidino]carbonyloxycamptothecin

Using 4-piperidinopiperidine (330 mg, 1.96 mmol) as the amine, the reaction followed by the after-treatment was carried out whereby the title compound (154 mg, 39.8%) was obtained.

M.P. 215°-218° C. (dec.).

$^1$H-NMR (in CDCl$_3$) δppm: 1.03 (3H, t, J=7 Hz), 1.40 (3H, t, J=7 Hz), 1.50-2.20 (16H, m), 2.50-2.60 (4H, m), 3.16 (2H, q, J=7 Hz), 4.38 (1H, br.s), 5.25 (2H, s), 5.52 (2H, ABq), 7.58 (1H, dxd, J=2 Hz, 9 Hz), 7.64 (1H, s), 7.83 (1H, d, J=2 Hz), 8.21 (1H, d, J=9 Hz).

IR $\nu_{max}^{KBr}$cm$^{-1}$: 3420, 2930, 1715, 1655, 1600, 1412, 1224, 1180, 1160, 1020, 800.

Elementary analysis as $C_{33}H_{38}N_4O_6 \cdot H_2O$: Calcd. C, 65.54; H, 6.67; N, 9.27; Found C, 65.28; H, 6.39; N, 9.39.

EXAMPLE 20

7-Ethyl-10-[N-methyl-N-(2-dimethylaminoethyl)-]aminocarbonyloxycamptothecin

Using N,N,N'-trimethylethylenediamine (200 mg, 1.96 mmol) as the amine, the reaction followed by the after-treatment was carried out whereby the title compound (168 mg, 48.9%) was obtained.

$^1$H-NMR (in CDCl$_3$) δppm: 1.03 (3H, t, J=7 Hz), 1.39 (3H, t, J=7 Hz), 1.84 (2H, q, J=7 Hz), 2.36 (6H, br.s), 2.64 (2H, q, J=6 Hz), 3.09, 3.22 (3H, s, s), 3.16 (2H, q, J=6 Hz), 3.58 (2H, t, J=7 Hz), 5.24 (2H, s), 5.27, 5.75 (2H, d, d, J=16 Hz), 7.26 (1H, s), 7.41 (1H, d, d, J=2 Hz, J=9 Hz), 7.62 (1H, d, J=2 Hz), 8.09 (1H, d, J=9 Hz).

EXAMPLE 21

7-Ethyl-10-[N-methyl-N-(1-methyl-4-piperidino)amino]carbonyloxycamptothecin

Using methyl-1-methyl-4-piperidylamine (250 mg, 1.95 mmol) as the amine, the reaction followed by the after-treatment was carried out whereby the title compound (221 mg, 60.8%) was obtained.

M.P. 159°–162° C. (dec.).

$^1$H-NMR (in CDCl$_3$) δppm: 1.03 (3H, t, J=7 Hz), 1.41 (3H, t, J=7 Hz), 1.80-2.15 (6H, m), 2.04 (3H, s), 3.06 (3H, s), 3.00-3.20 (6H, m), 4.12 (1H, q, J=7 Hz), 5.25 (2H, s), 5.52 (2H, ABq), 7.59 (1H, dxd, J=2 Hz, 8 Hz), 7.65 (1H, s), 7.85 (1H, d, J=2 Hz), 8.22 (1H, d, J=8 Hz).

IR $ν_{max}^{KBr}$cm$^{-1}$: 3420, 2940, 2800, 1745, 1720, 1656, 1600, 1405, 1365, 1322, 1232, 1188, 1160, 1112, 992, 822.

EXAMPLE 22

10-(4-Morpholino)carbonyloxycamptothecin

10-Chlorocarbonyloxycamptothecin (200 mg, 0.469 mol) was suspended in dry dioxane (50 ml). To this suspension was added morpholine (180 mg, 2.06 mmol), and the mixture was stirred for 3 hours at room temperature. The solvent was then removed by distillation under reduced pressure and the residue was subjected to column chromatography on silica gel for separation and purification whereby the title compound (111 mg, 49.9%) was obtained.

M.P. 277°–279° C.

$^1$H-NMR (in CDCl$_3$) δppm: 1.01 (3H, t, J=7 Hz), 1.87 (2H, q, J=7 Hz), 3.40-3.90 (8H, m), 5.18 (2H, s), 5.41 (2H, ABq), 7.46 (1H, dxd, J=2 Hz, 9 Hz), 7.52 (1H, s), 7.55 (1H, d, J=2 Hz), 8.07 (1H, d, J=9 Hz), 8.15 (1H, s).

IR $ν_{max}^{KBr}$cm$^{-1}$: 3400, 2960, 2920, 2850, 1750, 1718, 1653, 1598, 1415, 1360, 1222, 1190, 1146, 1118, 1055, 853, 746.

EXAMPLE 23

10-(4-Methyl-1-piperazino)carbonyloxycamptothecin

Using N-methylpiperazine (200 mg, 2.02 mmol) in place of morpholine in Example 22, the reaction followed by the after-treatment was carried out in the same manner as described in Example 22 whereby the title compound (141 mg, 61.3%) was obtained.

M.P. 279°–281° C. (dec.).

$^1$H-NMR (in CDCl$_3$) δppm: 1.02 (3H, t, J=7 Hz), 1.87 (2H, q, J=7 Hz), 2.32 (3H, s), 2.40 (4H, t, J=5 Hz), 3.50-3.90 (4H, m), 5.18 (2H, s), 5.41 (2H, ABq), 7.45 (1H, dxd, J=2 Hz, 8 Hz), 7.54 (1H, d, J=2 Hz), 7.66 (1H, s), 8.06 (1H, d, J=8 Hz), 8.14 (1H, s).

IR $ν_{max}^{KBr}$cm$^{-1}$: 3430, 2940, 2800, 1740, 1704, 1660, 1608, 1428, 1290, 1230, 1192, 1154, 1058, 1000, 838, 816.

EXAMPLE 24

7-Ethyl-10-(4-propyl-1-piperazino)carbonyloxycamptothecin

7-Ethyl-10-(1-piperazino)carbonyloxycamptothecin (80 mg, 0.156 mmol) was stirred in a mixed solvent of methylene chloride and ethanol with propyl bromide (200 μl) for 2 hours at room temperature in the presence of potassium carbonate (50 mg). Thereafter, insoluble matters were removed by filtration and the solvent was distilled off under reduced pressure from the filtrate. The residue was subjected to column chromatography on silica gel for purification whereby the title compound (30 mg, 34.7%) was obtained.

M.P. 210°–213° C. (dec.).

$^1$H-NMR (in CDCl$_3$) δppm: 0.93 (3H, t, J=7 Hz), 1.02 (3H, t, J=7 Hz), 1.38 (3H, t, J=7 Hz), 1.50-1.60 (2H, m), 1.87 (2H, q, J=7 Hz), 2.51 (2H, t, J=7 Hz), 3.11 (2H, q, J=7 Hz), 3.50-3.90 (8H, m), 5.16 (2H, s), 5.43 (2H, ABq), 7.45 (1H, dxd, J=2 Hz, 8 Hz), 7.50 (1H, s), 7.70 (1H, d, J=2 Hz), 8.07 (1H, d, J=8 Hz).

IR $ν_{max}^{KBr}$cm$^{-1}$: 3440, 2960, 2930, 1750, 1720, 1655, 1598, 1412, 1230, 1186, 1052, 1000, 818.

EXAMPLE 25

10-[4-(Isopropylcarbamoylmethyl)-1-piperazino]carbonyloxycamptothecin

To a solution of 10-chlorocarbonyloxycamptothecin (3.30 g, 4.5 mmol) in MeOH-CHCl$_3$ (210 ml–490 ml) containing 1.09 ml (11.1 mmol) of triethylamine was added with stirring N-isopropyl-1-piperazine acetamide (1.47 g, 7.8 mmol) in portions, and the mixture was stirred for 20 hours at room temperature. The reaction mixture was evaporated to dryness in vacuo and the residual material was passed through a silica gel column with 2%-MeOH-CHCl$_3$ as an eluent. The title compound was obtained in a yield of 0.31 g (11% yield) which was recrystallized from ethanol to give pale yellow needles.

M P. 204°–205° C. (dec.) [EtOH].

$^1$H-NMR (100 MHz, CDCl$_3$): 1.04 (t, 3H, J=6 Hz), 1.21 (d, 6H, J=6 Hz), 1.90 (q, 2H, J=6 Hz), 2.54-2.80 (m, 4H), 2.97-3.17 (s, 2H), 3.53-3.96 (m, 4H), 4.02-4.17 (m, 1H), 5.30 (s, 2H), 5.30 (d, 1H, J=15 Hz), 5.75 (d, 1H, J=15 Hz), 6.68-7.03 (m, 1H), 7.56 (q, 1H, J=3 Hz, 9 Hz), 7.64 (s, 1H), 7.66 (d, 1H, J=3 Hz), 8.19 (d, 1H, J=9 Hz), 8.25 (s, 1H).

MS m/e: 531 [M$^+$-CO$_2$].

Elementary analysis as C$_{30}$H$_{33}$N$_5$O$_7$: Calcd. C, 62.60; H, 5.78; N, 12.17; Found C, 62.47; H, 5.56; N, 12.00.

EXAMPLE 26

10-[4-(1-Piperidino)piperidino]carbonyloxycamptothecin

To a solution of 10-hydroxycamptothecin (364 mg, 1 mmol) in dry pyridine (25 ml) was added 1-chlorocarbonyl-4-piperidinopiperidine (395 mg, 1.97 mmol), and the mixture was stirred for 1 hour at room temperature. The reaction mixture was evaporated to dryness in vacuo and the residue was dissolved in CHCl$_3$ (200 ml). The solution was washed successively with a 7% aqueous solution of NaHCO$_3$ (100 ml), a saturated aqueous solution of NaCl (100 ml) and the CHCl$_3$ layer was dried with anhydrous MgSO$_4$, filtered, and evaporated in vacuo. The residual material was decolorized by passing it through a short silica gel column whereby 420 mg (75% in yield) of the title compound was obtained.

M.P. 201° C. (dec.).

MS m/z: 514, 195.

$^1$H-NMR (100 MHz, CDCl$_3$) δppm: 1.03 (t, 3H, J=7 Hz), 1.29-1.88 (m, 10H), 1.89 (q, 2H, J=7 Hz), 2.61 (br., 5H), 2.83-3.22 (m, 2H), 3.88-4.09 (s, 1H), 4.20-4.59 (m, 2H), 5.25 (s, 2H), 5.27 (d, 1H, J=16 Hz), 5.71 (d, 1H, J=16 Hz), 7.52 (dd, 1H, J=3 Hz, 9 Hz), 7.59 (s, 1H), 7.60(d, 1H, J=3 Hz), 8.12 (d, 1H, J=9 Hz), 8.22 (s, 1H).
IR $\nu_{max}^{KBr}$cm$^{-1}$: 1752, 1719, 1656, 1600, 1226, 1190, 1146.

EXAMPLE 27

7-Chloro-10-[4-(1-piperidino)-1-piperidino]carbonyloxycamptothecin

7-Chloro-10-hydroxycamptothecin (110 mg, 0.280 mmol) and 1-chlorocarbonyl-4-piperidinopiperidine (100 mg, 0.42 mmol) were dissolved in anhydrous pyridine (12 ml) and the mixture was stirred for 1 hour at room temperature. The reaction mixture was evaporated to dryness in vacuo, and the residue was dissolved in CHCl$_3$ (100 ml). The CHCl$_3$ solution was shaken with a 7% aqueous solution of NaHCO$_3$ (100 ml), a saturated aqueous solution of NaCl, dried with MgSO$_4$, filtered and then evaporated to dryness in vacuo. The residual material was purified by way of column chromatography on silica gel with 2% MeOH-CHCl$_3$ as an eluent to give 110 mg (66.6% in yield) of the title compound, which gave 52 mg (31.1% yield) of pale yellow needles after recrystallization from ethanol.
$^1$H-NMR (in CDCl$_3$) δppm: 1.04 (3H, t, J=7 Hz), 1.55–1.70 (13H, m), 1.99 (2H, q, J=7 Hz), 3.64 (1H, m), 5.32 (2H, s), 5.55 (2H, dxd, J=15 Hz), 7.63 (1H, s), 7.66 (1H, dxd, J=2 Hz, 9 Hz), 8.04 (1H, d, J=2 Hz), 8.24 (1H, d, J=9 Hz).
MS m/e: 592[M$^+$], 594[M$^+$+2].
IR $\nu_{max}^{KBr}$cm$^{-1}$: 3350, 2920, 1745, 1700, 1650, 1595, 1420, 1220, 1152, 1048, 842.

EXAMPLE 28

7-Ethyl-10-[4-(1-piperidino)-1-piperidino]carbonyloxycamptothecin

7-Ethyl-10-hydroxycamptothecin (790 mg, 2.01 mmol) and 1-chlorocarbonyl-4-piperidinopiperidine (910 mg, 3.95 mmol) were dissolved in anhydrous pyridine (50 ml), and the mixture was stirred for 1 hour at room temperature. The reaction mixture was evaporated to dryness in vacuo and the residue was dissolved in CHCl$_3$ (200 ml). The solution was washed successively with a 7% aqueous solution of NaHCO$_3$ (200 ml), a saturated aqueous solution NaCl, and the CHCl$_3$ layer was dried with MgSO$_4$, filtered, and evaporated in vacuo. The residual material was decolorized by passing it through a short silica gel column whereby 1.11 g (94.8% in yield) of the title compound was obtained as a pale yellow mass, which was recrystallized from ethanol (ca. 60 ml) to give colorless needles (750 mg, 63.5% in yield).

EXAMPLE 29

7-Ethyl-10-[4-(isopropylcarbamoylmethyl)-1-piperazino]carbonyloxycamptothecin

7-Ethyl-10-hydroxycamptothecin (500 mg, 1.27 mmol) and 1-chlorocarbonyl-4-(isopropylcarbamoylmethyl)piperazine (633 mg, 2.56 mmol) were dissolved in anhydrous pyridine (30 ml) and the mixture was stirred for 15 hours at room temperature. The reaction mixture was evaporated to dryness in vacuo and the residue was shaken with CHCl$_3$ (300 ml) and a 7% aqueous solution of NaHCO$_3$ (300 ml). The CHCl$_3$ layer was separated, washed with a saturated aqueous solution of NaCl (300 ml), dried with MgSO$_4$, filtered, and then evaporated to dryness in vacuo. The residual material was purified by way of column chromatography on silica gel with 2% MeOH-CHCl$_3$ as an eluent whereby a pale yellow mass was obtained, which was recrystallized from ethanol to give 600 mg (75.9% yield) of the title compound as pale yellow needles.

EXAMPLE 30

7-Ethyl-10-[4-(pyrrolidinocarbonylmethyl)-1-piperazino]carbonyloxycamptothecin

To a suspension of 10-chlorocarbonyloxy-7-ethylcamptothecin (300 mg, 0.66 mmol) in dry dioxane (50 ml) was added 1-pyrrolidinocarbonylmethylpiperazine (430 mg, 2.2 mmol), and the mixture was stirred for 12 hours at room temperature. The reaction mixture was evaporated to dryness in vacuo and residual material was purified by way of column chromatography on silica gel with 2% MeOH-CHCl$_3$ as an eluent whereby 180 mg (45% in yield) of the title compound was obtained.
M.P. 165.5°–166.5° C. (dec.) [EtOH].
$^1$H-NMR (in CDCl$_3$) δppm: 1.03 (3H, t, J=8 Hz), 1.43 (3H, t, J=8 Hz), 1.75 (2H, q, J=8 Hz), 1.93 (4H, m), 2.73 (4H, m), 3.20 (2H, q, J=8 Hz), 3.26 (2H, s), 3.53 (4H, t, J=6 Hz), 3.80 (4H, m), 5.30 (2H, s), 5.33, 5.80 (1H, d,d, J=16.5 Hz), 7.58 (1H, d, J=3 Hz), 7.70 (2H, m), 7.90 (1H, d, J=3 Hz), 8.28 (1H, d, J=3 Hz).
Elementary analysis as C$_{33}$H$_{37}$N$_5$O$_7$.H$_2$O: Calcd. C, 62.55; H, 6.20; N, 11.05; Found C, 62.45; H, 6.05; N, 11.12.

EXAMPLE 31

7-Ethyl-10-[4-(morpholinocarbonylmethyl)-1-piperazinocarbonyloxycamptothecin

To a suspension of 10-chlorocarbonyloxy-7-ethylcamptothecin (300 mg, 0.66 mmol) in dry dioxane (50 ml) was added 1-morpholinocarbonylmethylpiperazine (470 mg, 2.2 mmol), and the mixture was stirred for 18 hours at room temperature. The reaction mixture was evaporated to dryness in vacuo and the residual material was purified by way of column chromatography on silica gel with 2% MeOH-CHCl$_3$ as an eluent whereby 230 mg (55% in yield) of the title compound was obtained, which gave pale yellow needles by recrystallization from ethanol.
M.P. 205.5°–208° C. (dec.) [EtOH].
$^1$H-NMR (in CDCl$_3$) δppm: 1.07 (3H, t, J=8 Hz), 1.43 (3H, t, J=8 Hz), 1.86 (2H, q, J=8 Hz), 2.70 (4H, m), 3.28 (2H, q, J=8 Hz), 3.33 (2H, s), 3.70 (12H, br.s), 5.30 (2H, s), 5.35, 5.83 (2H, dxd, J=16.5 Hz), 7.63 (1H, d, J=3 Hz), 7.93 (1H, d, J=3 Hz), 8.32 (1H, d, J=9 Hz).
Elementary analysis as C$_{33}$H$_{37}$N$_5$O$_8$.½H$_2$O: Calcd. C, 61.86; H, 5.98; N, 10.93; Found C, 62.06; H, 5.78; N, 10.94.

EXAMPLE 32

7-Ethyl-10-[(2-carboxy)-1-pyrrolidino]carbonyloxycamptothecin

To a solution of 10-chlorocarbonyloxy-7-ethylcamptothecin (1.88 g, 4.12 mmol) in anhydrous pyridine (100 ml), was added L-proline (568 mg, 4.94 mmol), and the mixture was stirred for 48 hours at room temperature. The reaction mixture was evaporated to dryness in vacuo and the residue was purified by way of column chromatography on silica gel with 2% MeOH-CHCl$_3$ as an eluent whereby 610 mg (27.8% in yield) of the title compound was obtained as yellow crystals.

$^1$H-NMR (in DMSO-d$_6$) δppm: 0.88 (3H, t, J=7 Hz), 1.29 (3H, t, J=7 Hz), 1.80–2.20 (4H, m), 2.90–3.60 (6H, m), 5.24 (2H, s), 5.41 (2H, s), 6.47 (1H, s, D$_2$O-exchangeable), 7.23 (1H, s), 7.27–8.03 (3H, m), 8.31 (1H, s).

MS m/e: 504 [M$^+$-29], 489 [M$^+$-44].

EXAMPLE 33

10-[4-isopropylcarbamoylmethyl)-1-piperazino]carbonyloxy-7-propylcamptothecin

To a solution of 10-hydroxy-7-propylcamptothecin (390 mg, 1 mmol) in dry pyridine (50 ml) was added 1-chlorocarbonyl-4-(isopropylcarbamoylmethyl)piperazine (444 mg, 1.8 mmol), and the mixture was stirred for 16 hours at room temperature. The reaction mixture was evaporated to dryness in vacuo and the residue was dissolved in CHCl$_3$ (250 ml). The solution was washed successively with a 7% aqueous solution of NaHCO$_3$ (350 ml) and a saturated aqueous solution of NaCl (200 ml) dried with anhydrous MgSO$_4$, filtered, and then evaporated to dryness in vacuo. The residue was purified by way of column chromatography on silica gel with 2% MeOH-CHCl$_3$ as an eluent whereby 462 mg (75% in yield) of the title compound was obtained.

M.P. 226°–229° C.

MS m/z: 573 [M$^+$-44], 487 [base, 573-(CH$_3$)$_2$CHNHCO].

$^1$H-NMR (100 MHz, CDCl$_3$) δppm: 1.04 (t, 3H, J=6 Hz), 1.10 (t, 3H, J=6 Hz), 1.22 (d, 6H, J=7 Hz), 1.70–2.11 (m, 4H), 2.51–2.87 (m, 4H), 2.90–3.30 (m, 4H), 3.52–3.93 (m, 4H), 3.98 (s, 1H), 3.99–4.35 (m, 1H), 5.24 (s, 2H), 5.29 (d, 1H, J=16 Hz), 5.75 (d, 1H, J=16 Hz), 6.70–7.45 (m, 1H), 7.55 (dd, 1H, J=2 Hz, 9 Hz), 7.62 (s, 1H), 7.78 (d, 1H, J=2 Hz), 8.18 (d, 1H, J=9 Hz).

IR $\nu_{max}^{KBr}$cm$^{-1}$: 1753, 1720, 1656, 1592, 1227, 1205, 1178, 1155.

EXAMPLE 34

7-Butyl-10-[4-(1-piperidino)-1-piperidino]carbonyloxycamptothecin

7-Butyl-10-hydroxycamptothecin (386 mg, 0.9 mmol) and 4-piperidinopiperidino-1-carbonyl chloride (320 mg, 1.4 mmol) were dissolved in anhydrous pyridine (ca. 20 ml), and the mixture was stirred for 45 min. at room temperature. The reaction mixture was evaporated to dryness in vacuo and the residual material was purified by way of column chromatography on silica gel with 2% MeOH-CHCl$_3$ as an eluent whereby 360 mg (66.6% in yield) of the title compound was obtained which was recrystallized from ethanol to give pale yellow needles (137 mg, 24% in yield).

M.P. 204–207 (dec.) [EtOH].

$^1$H-NMR (100 MHz, CDCl$_3$) δppm: 0.90–1.22 (m, 6H), 1.32–2.32 (m, 16H), 2.51–2.90 (m, 5H), 2.91–3.38 (m, 4H), 4.04 (s, 1H), 4.24–4.73 (m, 2H), 5.25 (s, 2H), 5.30 (d, 1H, J=16 Hz), 5.76 (d, 1H, J=16 Hz), 7.56 (dd, 1H, J=3 Hz, 9 Hz), 7.65 (s, 1H), 7.78 (d, 1H, J=3 Hz), 8.18 (d, 1H, J=9 Hz).

IR $\nu_{max}^{KBr}$cm$^{-1}$: 1754, 1719, 1653, 1596, 1224, 1196, 1180, 1153.

MS m/e: 614 [M$^+$], 570 [M$^+$—CO$_2$].

Elementary analysis as C$_{35}$H$_{42}$O$_6$N$_2$: Calcd. C, 68.38; H, 6.89; N, 9.12; Found C, 68.09; H, 6.87; N, 8.83.

EXAMPLE 35

7-Ethyl-10-(4-methyl-1-piperazino)carbonyloxycamptothecin hydrochloride

7-Ethyl-10-(4-methyl-1-piperazino)carbonyloxycamptothecin (500 mg, 0.97 mmol) obtained in Example 13 was dissolved in ethanol (10 ml) containing 9 ml of 0.1N HCl, and the solution was passed through a filter (0.5 μm in pore size, Millex-SR). The filtrate was evaporated to dryness in vacuo at 40° C. and the residual yellow powder was recrystallized from absolute ethanol whereby 373 mg (74% in yield) of the title compound was obtained as yellow needles. The salt was freely soluble in water and an aqueous solution of the salt (25 mg/ml) showed a pH value of about 6.

EXAMPLE 36

7-Ethyl-10-(1-piperazino)carbonyloxycamptothecin sulfate

To an ice-cooled suspension in distilled water (18 ml) of 7-ethyl-10-(1-piperazino)carbonyloxycamptothecin (1.00 g, 1.98 mmol) obtained in Example 12 was added 1/10N H$_2$SO$_4$ (17.9 ml, 0.895 mmol), and the suspended solution was stirred vigorously for 5 minutes under cooling in an ice bath. The solution was passed through a filter (0.22 μm, SLGS 025 OS) and the filtrate was lyophilized overnight (−40°–+25° C., 10 mmHg) whereby 985 mg (96% in yield) of the title compound was obtained as a pale yellow amorphous solid.

EXAMPLE 37

7-Ethyl-10-[4-(1-piperidino)-1-piperidino]carbonyloxycamptothecin hydrochloride

To an ice-cooled suspension in distilled water (15 ml) of 7-ethyl-10-[1-(4-piperidino)piperidino]carbonyloxycamptothecin (1.00 g, 1.7 mmol) obtained in Example 19 was added 1/10N HCl (15.3 ml, 1.53 mmol), and the suspension was stirred vigorously for 5 minutes under cooling in an ice bath. The solution was passed through a filter (0.22 μm, SLGS 025 OS) and the filtrate was lyophilized overnight (−40°–25° C., 10 mmHg) whereby 950 mg (89.8% in yield) of the title compound was obtained as a pale yellow amorphous solid.

IR $\nu_{max}^{KBr}$cm$^{-1}$: 3400, 2950, 2650, 1740(sh), 1710, 1650, 1595, 1410, 1220, 1180, 1040.

EXAMPLE 38

7-Ethyl-10-[4-(1-piperidino)-1-piperidino]carbonyloxycamptothecin sulfate

To an ice-cooled suspension in distilled water (15 ml) of 7-ethyl-10-[1-(4-piperidino)piperidino]carbonyloxycamptothecin (1.00 g, 1.7 mmol) obtained in Example 19 was added 1/10N H$_2$SO$_4$ aq (15.3 ml, 7.65 mmol), and the suspended solution was stirred vigorously for 5 minutes under cooling in an ice bath. The solution was passed through a filter (0.22 μm, SLGS 025 OS) and the filtrate was lyophilized overnight (−40°–+25° C., 10 mmHg) whereby 970 mg (90% in yield) of a pale yellow amorphous solid which was recrystallized from absolute ethanol to give pale yellow needles (776 mg, 71.8% in yield).

M.P. 205°–207° C. (dec.) [EtOH].

IR $\nu_{max}^{KBr}$cm$^{-1}$: 3400, 2920, 1740(sh), 1750, 1650, 1595, 1410, 1215, 1180, 1150, 1100, 1010.

Elementary analysis as $C_{33}H_{38}N_4O_6 \cdot \frac{1}{2}H_2SO_4 \cdot 5H_2O$:
Calcd. C, 58.22; H, 6.52; N, 8.23; Found C, 58.11; H, 6.24; N, 8.23.

EXAMPLE 39

7-Ethyl-10-[4-(isopropylcarbamoylmethyl)-1-piperazino]carbonyloxycamptothecin sulfate To an ice-cooled suspension in distilled water (14 ml) of 7-ethyl-10-[4-(isopropylcarbamoylmethyl)-1-piperazino]carbonyloxycamptothecin (1.00 g, 1.6 mmol) obtained in Example 18 was added 1/10 N $H_2SO_4$ (14.5 ml, 7.25 mmol), and the suspension was stirred vigorously for 5 minutes under cooling in an ice bath. The solution was passed through a filter (0.22 μm, SLGS 025 OS) and the filtrate was lyophilized overnight ($-40°-+25°$ C., 10 mmHg) whereby 965 mg (96% in yield) of the title compound was obtained as a pale yellow amorphous solid.

EXAMPLE 40

7-Ethyl-10-[4-(isopropylcarbamoylmethyl)-1-piperazino]carbonyloxycamptothecin methanesulfonate To a solution of 7-ethyl-10-[4-(isopropylcarbamoyl-methyl)-1-piperazino]carbonyloxycamptothecin (200 mg, 0.32 mmol) obtained in Example 18 in ethanol (100 ml) was added 1/10N methanesulfonic acid (3 ml, 0.3 mmol), and the resulting yellow solution was passed through a filter (0.5 μm, Millex-SR). The filtrate was evaporated to dryness in vacuo at about 40° C. The residual material was recrystallized from ethanol to give 520 mg (72% in yield) of the title compound as yellow prisms.

IR $\nu_{max}^{KBr}$cm$^{-1}$: 3450, 2950, 1720, 1650, 1600, 1420, 1195, 1050, 960.

EXAMPLE 41

7-Ethyl-10-[(2-carboxy)-1-pyrrolidino]carbonyloxycamptothecin sodium salt

To an ice-cooled suspension in distilled water (15 ml) of 7-ethyl-10-[(2-carboxy)-1-pyrrolidino]carbonyloxycamptothecin (1.00 g, 1.88 mmol) obtained in Example 32 was added 1/10N NaOH (16.9 ml, 1.69 mmol), and the suspension was stirred vigorously for 5 minutes under cooling in ice-bath. The solution was allowed to pass through a filter (0.22 μm, SLGS 0.25 OS) and the filtrate was lyophilized overnight ($-40°$ C.$-+25°$ C., 10 mmHg) whereby 872 mg (85.5% in yield) of the title compound was obtained as a pale yellow amorphous solid.

M.P. 232°–234° C. (dec.) [EtOH].

EXAMPLE 42

11-[4-(1-Piperidino)-1-piperidino]carbonyloxycamptothecin

11-Hydroxycamptothecin (35 mg, 0.096 mmol) and 1-chlorocarbonyl-4-piperidinopiperidine (45 mg, 0.195 mmol) were dissolved in anhydrous pyridine (2 ml), and the mixture was stirred for 45 minutes at room temperature. After removal of the solvent by evaporation, the residual material was purified by way of preparative thin layer chromatography using 10% MeOH-CHCl$_3$ as a solvent whereby 27 mg (50.4% in yield) of the title compound was obtained.

$^1$H-NMR (in CDCl$_3$) δppm: 1.03 (3H, t, J=7 Hz), 1.60–2.50 (18H, m), 4.43 (1H, br.s), 5.29 (2H, s), 5.54 (2H, d,d, J=15 Hz), 7.52 (1H, d,d, 2 Hz, 8 Hz), 7.65 (1H, s), 7.84–7.95 (2H, m), 8.38 (1H, s).
MS m/e: 558 [M+].

EXAMPLE 43

11-[4-(Isopropylcarbamoylmethyl)-1-piperazino]carbonyloxycamptothecin

11-Hydroxycamptothecin (35 mg, 0.096 mmol) and 1-chlorocarbonyl-4-(isopropylcarbamoylmethyl)piperazine (50 mg, 0.202 mmol) were dissolved in dry pyridine (2 ml), and the mixture was stirred for 16 hours at room temperature. After removal of the solvent by evaporation, the residual material was purified by way of preparative thin layer chromatography using 10% MeOH-CHCl$_3$ as a solvent whereby 37 mg (68% in yield) of the title compound was obtained.

EXAMPLE 44

7-Ethyl-11-[1-(4-piperidino)piperidino]carbonyloxycamptothecin

7-Ethyl-11-hydroxycamptothecin (45 mg, 0.114 mmol) and 1-chlorocarbonyl-4-piperidinopiperidine (53 mg, 0.228 mmol) were dissolved in dry pyridine (3 ml), and the mixture was stirred for 1 hour at room temperature. After removal of the solvent by evaporation, the residual material was purified by way of preparative thin layer chromatography using 10% MeOH-CHCl$_3$ as a solvent whereby 36 mg (53.8% in yield) of the title compound was obtained.

$^1$H-NMR (in CDCl$_3$) δppm: 1.30 (3H, t, J=7 Hz), 1.41 (3H, t, J=7 Hz), 1.55–2.55 (20H, m), 3.15 (2H, q, J=7 Hz), 4.40 (1H, br.s), 5.26 (2H, s), 5.53 (2H, dxd, 16 Hz), 7.50 (1H, m), 7.65 (1H, s), 7.92 (1H, d, J=2 Hz), 8.12 (1H, d, J=9 Hz).

EXAMPLE 45

11-(4-Ethyl-1-piperazino)carbonyloxycamptothecin

11-Hydroxycamptothecin (82 mg, 0.225 mmol) and 1-chlorocarbonyl-4-ethylpiperazine (65 mg, 0.369 mmol) were dissolved in dry pyridine (5 ml), and the mixture was stirred for 2 hours at room temperature. The reaction mixture was evaporated to dryness in vacuo and the residual material was dissolved in CHCl$_3$ (25 ml). The CHCl$_3$ solution was washed successively with a 7% aqueous solution of NaHCO$_3$ (50 ml), a saturated aqueous solution of NaCl, dried with anhydrous MgSO$_4$, filtered, and then evaporated to dryness in vacuo. The residue was purified by way of column chromatography on silica gel with 2% MeOH-CHCl$_3$ as an eluent whereby 73 mg (64% in yield) of the title compound was obtained as a pale yellow solid.

$^1$H-NMR (in CDCl$_3$) δppm: 1.04 (3H, t, J=7 Hz), 1.21 (3H, t, J=7 Hz), 1.98 (2H, q, J=7 Hz), 2.40 (2H, q, J=7 Hz), 3.25–3.45 (8H, m), 5.28 (2H, s), 5.52 (2H, dxd, J=15 Hz), 7.50 (1H, dxd, J=2 Hz, 9 Hz), 7.56 (1H, s), 7.85–7.95 (2H, m), 8.35 (1H, s).
MS m/e: 504 [M+].

IR $\nu_{max}^{KBr}$cm$^{-1}$: 3380, 2920, 1715, 1652, 1600, 1403, 1210 1192, 1150, 1040, 900.

REFERENTIAL EXAMPLE 1

7-Chloro-10-hydroxycamptothecin (A) Camptothecin 1-oxide (115 mg, 0.315 mmol) was dissolved in dry dimethylformamide (35 ml). Phosphoryl chloride (253 mg, 1.64 mmol) was added dropwise to the solution with stirring. After continuously stirring for 1.5 hours at room temperature, the reaction mixture was evaporated to dryness in vacuo and the residual material was washed with MeOH (10 ml) whereby 96 mg (80% in yield) of the title compound was obtained as a pale yellow solid.

M.P. 271°–273° C. [MeOH-CHCl₃-n-hexane].

MS m/e: 382 [M+] 384 [M++2].

(B) 7-Chlorocamptothecin (2.00 g, 5.23 mmol) was dissolved in acetic acid (400 ml). To the solution was added an aqueous solution of 30% hydrogen peroxide (120 ml), and the mixture was heated at 80°–85° C. in a water bath for 5 hours. The reaction mixture was concentrated to a half of its original volume and the concentrated solution was poured into ice-water (5 l). The resulting precipitate was collected on a filter by suction and dried in vacuo for 6 hours at 60° C. over P₂O₅ as a drying agent whereby 670 mg (32.1% in yield) of 7-chlorocamptothecin 1-oxide was thus obtained.

7-Chlorocamptothecin 1-oxide (335 mg, 0.84 mmol) was dissolved in dioxane (1 l) containing 8.5 ml of N/10 H₂SO₄ and the mixture was irradiated with the light from a 450 W Hg high pressure lamp for 13 minutes under cooling with water. The resulting mixture was evaporated to dryness in vacuo and the residue was dissolved in 20% MeOH-CHCl₃ (20 ml). The solution was washed with water (500 ml) and the precipitate was collected on a filter by suction whereby 110 mg (32.8% in yield) of the title compound was obtained as pale yellow needles after recrystallizing from MeOH-n-hexane-CHCl₃.

¹H-NMR (in CDCl₃) δppm: 1.04 (3H, t, J=7 Hz), 1.99 (2H, q, J=7 Hz), 5.32 (2H, s), 5.31, 5.68 (2H, d, d, J=16 Hz), 7.56 (1H, dxd, J=2 Hz, 9 Hz), 7.95 (1H, d, J=2 Hz), 8.23 (1H, d, J=9 Hz).

MS m/e: 398 [M+], 400 [M++2].

REFERENTIAL EXAMPLE 2

7-Ethyl-11-hydroxycamptothecin

11-Hydroxycamptothecin (100 mg, 0.27 mmol) was suspended in water (3 ml). To the suspension, Conc. H₂SO₄ (1.2 ml) was added until the hydroxycamptothecin was dissolved in the propionaldehyde (50 mg, 0.862 mmol) and FeSO₄.7H₂O (70 mg, 0.25 mmol) were added to the solution and then 30% H₂O₂ (120 μl, 0.85 mmol) was added dropwise to the mixture under ice-cooling with stirring. After addition of the hydrogen peroxide, the mixture was stirred for 2 hours at room temperature. The reaction mixture was poured into ice-water (250 ml), and the precipitate in the solution was extracted with CHCl₃ (200 ml×2). The CHCl₃ layer was washed with a saturated aqueous solution of NaCl, dried with MgSO₄, filtered, and then evaporated to dryness in vacuo. The residual material was recrystallized from ethanol to give 60 mg (59.3% in yield) of the title compound as pale yellow needles.

¹H-NMR (in CDCl₃-CD₃OH) δppm: 1.03 (3H, t, J=7 Hz), 1.41 (3H, t, J=7 Hz), 1.94 (2H, q, J=7 Hz), 3.20 (2H, q, J=7 Hz), 5.29, 5.70 (1H, 1H, dxd, J=16 Hz), 5.23 (2H, s), 7.33 (1H, dd, J=2 Hz, 9 Hz), 7.46 (1H, d, J=2 Hz), 7.60, (1H, s), 8.05 (1H, d, J=9 Hz).

IR ν$_{max}^{KBr}$cm⁻¹: 3200, 2975, 2925, 1735, 1650, 1590, 1570, 1460, 1250, 1230, 1155, 1110, 1030.

It is understood that the preceeding representative examples may be varied within the scope of the present specification, both as to the reactants and conditions, by one skilled in the art to achieve essentially the same results.

As many apparently widely different embodiments of the present invention may be made without departing from the spirit and scope thereof, it is to be construed that the present invention is not limited to the specific embodiments thereof as defined in the appended claims.

What is claimed is:

1. Camptothecin derivatives of the formula:

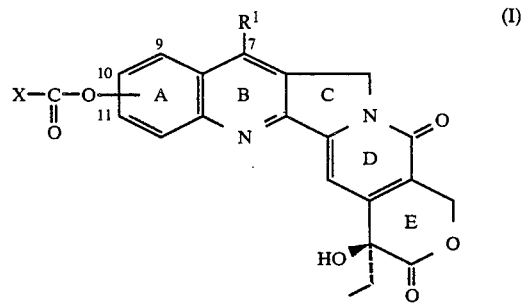

wherein R¹ is a hydrogen atom, a halogen atom or an alkyl group with 1–4 carbon atoms and X is a chlorine atom or —NR²R³ where R² and R³ are the same or different and each represents a hydrogen atom, a substituted or unsubstituted alkyl group with 1–4 carbon atoms or a substituted or unsubstituted group selected from the group consisting of cyclopentyl, cyclohexyl, N-methylpiperidyl-(4), 2-pyrrolidyl, phenyl, tolyl, xylyl, pyridyl-2 and 2-methylpyridyl-(4), with the proviso that when both R² and R³ are the substituted or unsubstituted alkyl groups, they may be combined together with the nitrogen atom, to which they are bonded, to form a heterocyclic ring selected from the group consisting of pyrrolidine, piperidine, 2-oxapyrrolidine, morpholine, thiomorpholine and 4-R⁴ piperizine rings in which R⁴ is a hydrogen atom, a substituted or unsubstituted alkyl group with 1–4 carbon atoms or a substituted or unsubstituted phenyl group and wherein the grouping —O—CO—X is bonded to a carbon atom located in any of the 9-, 10- and 11-positions in the ring A, and ammonium salts or alkali metal salts thereof.

2. The camptothecin derivatives according to claim 1, wherein R², R³ or R⁴ in case of the alkyl group is substituted by one or more substituents selected from the following atoms and/or groups:

| | |
|---|---|
| —F, —Cl, —Br and —I, | (A) |
| —OH and —OR⁵, | (B) |
| —COOR⁶, —SO₃R⁶ and —PO₃(R⁶)₂, | (C) |

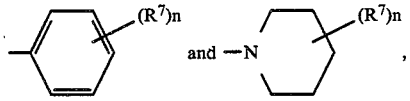

(D)

| | |
|---|---|
| —NR⁸R⁹ and —CONR⁸R⁹, and | (E) |
| —Q—A—OR⁵, —Q—A—NR⁸R⁹ and —Q—A—Q—R⁵ | (F) | wherein R⁵ is an alkyl group with 1–4 carbon atoms or a phenyl group which may be substituted by a halogen atom or an alkyl group with 1–4 carbon atoms, R⁶ is a hydrogen atom or an alkyl group with 1–4 carbon atoms, R⁷ is a hydrogen atom, a halogen atom, an alkyl group with 1–4 carbon atoms or an alkoxy group with 1–4 carbon atoms, n is an integer of 1–3, R⁸ and R⁹ are the same or different and each represents a hydrogen atom or an alkyl group with 1–4 carbon atoms with the proviso that when both $R^8$ and $R^9$ are the alkyl groups, they may be combined together with the nitrogen atom, to which they are bonded, to from a heterocyclic ring selected from the group consisting of pyrrolidine, piperidine, 2-oxapyrrolidine, morpholine and 4-$R^4$-piperazine rings, Q is the grouping —O—CO— or —CO—O—, and A is a straight or branched chain alkylene group with 1–4 carbon atoms.

3. Camptothecin derivatives according to claim 1, which are 9-chlorocarbonyloxy-7-$R^1$-camptothecins.

4. Camptothecin derivatives according to claim 1, which are 10-chlorocarbonyloxy-7-$R^1$-camptothecins.

5. Camptothecin derivatives according to claim 1, which are 11-chlorocarbonyloxy-7-$R^1$camptothecins.

6. Camptothecin derivatives according to claim 1, which are 9-(4-$R^4$-1-piperazino)carbonyloxy-7-$R^1$-camptothecins.

7. Camptothecin derivatives according to claim 1, which are 9-(1-piperazino)carbonyloxy-7-$R^1$-camptothecins.

8. Camptothecin derivatives according to claim 1, which are 9-[(4-$C_{1-4}$alkylcarbamoylmethyl)-1-piperazino]carbonyloxy-7-$R^1$-camptothecins.

9. Camptothecin derivatives according to claim 1, which are 9-[4-(1-piperidino)-1-piperidino]carbonyloxy-7-$R^1$-camptothecins.

10. Camptothecin derivatives according to claim 1, which are 10-(di-$C_{1-4}$alkylamino)carbonyloxy-7-$R^1$-camptothecins.

11. Camptothecin derivatives according to claim 1, which are 10-[N-(di-$C_{1-4}$alkylamino-$C_{1-4}$alkyl)]aminocarbonyloxy-7-$R^1$-camptothecins.

12. Camptothecin derivatives according to claim 1, which are 10-[N-$C_{1-4}$alkyl-N-(di-$C_{1-4}$alkylamino-$C_{1-4}$alkyl)]aminocarbonyloxy-7-$R^1$-camptothecins.

13. Camptothecin derivatives according to claim 1, which are 10-[N-$C_{1-4}$alkyl-N-(1-$C_{1-4}$alkyl-4-piperidino)amino]carbonyloxy-7-$R^1$-camptothecins.

14. Camptothecin derivatives according to claim 1, which are 10-[4-$R^4$-1-piperazino]carbonyloxy-7-$R^1$-camptothecins.

15. Camptothecin derivatives according to claim 1, which are 10-(1-piperazino)carbonyloxy-7-$R^1$-camptothecins.

16. Camptothecin derivatives according to claim 1, which are 10-(4-$C_{1-4}$alkyl-1-piperazino)carbonyloxy-7-$R^1$-camptothecins.

17. Camptothecin derivatives according to claim 1, which are 10-(4-phenyl-1-piperazino)carbonyloxy-7-$R^1$-camptothecins.

18. Camptothecin derivatives according to claim 1, which are 10-(4-benzyl-1-piperazino)carbonyloxy-7-$R^1$-camptothecins.

19. Camptothecin derivatives according to claim 1, which are 10-[(4-$C_{1-4}$alkylcarbamoylmethyl)-1-piperazino]carbonyloxy-7-$R^1$-camptothecins.

20. Camptothecin derivatives according to claim 1, which are 10-[4-(piperidino)-1-piperidino]carbonloxy-7-$R^1$-camptothecins.

21. Camptothecin derivatives according to claim 1, which are 10-(4-morpholino)carbonyloxy-7-$R^1$-camptothecins.

22. Camptothecin derivatives according to claim 1, which are 11-(4-$R^4$-1-piperazino)carbonyloxy-7-$R^1$-camptothecins.

23. Camptothecin derivatives according to claim 1, which are 11-(4-$C_{1-4}$alkyl-1-piperazino)carbonyloxy-7-$R^1$-camptothecins.

24. Camptothecin derivatives according to claim 1, which are 11-[(4-$C_{1-4}$alkylcarbamoylmethyl)-1-piperazino]carbonyloxy-7-$R^1$-camptothecins.

25. Camptothecin derivatives according to claim 1, which are 11-[4-(1-piperidino)-1-piperidino]carbonyloxy-7-$R^1$-camptothecins.

* * * * *

UNITED STATES PATENT AND TRADEMARK OFFICE

CERTIFICATE EXTENDING PATENT TERM
UNDER 35 U.S.C. § 156

PATENT NO.      :   4,604,463

ISSUED          :   August 5, 1986

INVENTOR(S)     :   Tadashi Miyasaka et al.

PATENT OWNER    :   Kabushiki Kaisha Yakult Honsha

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,141 days from July 5, 2004, the original expiration date of the patent, subject to the payment of maintenance fees as provided by law, with all rights pertaining thereto as provided by 35 U.S.C. § 156(b).

I have caused the seal of the Patent and Trademark Office to be affixed this 27th day of February 1998.

Bruce A. Lehman
Assistant Secretary of Commerce and
 Commissioner of Patents and Trademarks